(12) United States Patent
Krespi et al.

(10) Patent No.: US 7,544,204 B2
(45) Date of Patent: Jun. 9, 2009

(54) CONTROL OF HALITOSIS-GENERATING AND OTHER MICROORGANISMS IN THE NON-DENTAL UPPER RESPIRATORY TRACT

(75) Inventors: Yosef Krespi, New York, NY (US); Ashutosh Kacker, New York, NY (US)

(73) Assignee: Valam Corporation, New York, NY (US)

( * ) Notice: Subject to any disclaimer, the term of this patent is extended or adjusted under 35 U.S.C. 154(b) by 383 days.

(21) Appl. No.: 11/066,729

(22) Filed: Feb. 25, 2005

(65) Prior Publication Data

US 2006/0047329 A1    Mar. 2, 2006

Related U.S. Application Data

(63) Continuation of application No. 10/929,694, filed on Aug. 30, 2004, now abandoned.

(60) Provisional application No. 60/511,549, filed on Oct. 15, 2003.

(51) Int. Cl.
*A61N 5/06* (2006.01)
(52) U.S. Cl. .............................. 607/88; 607/92; 128/898
(58) Field of Classification Search ............. 607/88–95, 607/134; 15/105; 128/898; 606/88–94, 606/134
See application file for complete search history.

(56) References Cited

U.S. PATENT DOCUMENTS 4,689,215 A    8/1987   Ratcliff (Continued)

FOREIGN PATENT DOCUMENTS

WO    WO 3045403 A1 *   6/2003

OTHER PUBLICATIONS

C. E. Kazor et al "Diversity of Bacterial Populations.." Journal of Clinical Microbiology, Feb. 2003, vol. 41, No. 2, p. 558-563.

(Continued)

*Primary Examiner*—John P Leubecker
*Assistant Examiner*—Victoria W Chen
(74) *Attorney, Agent, or Firm*—K&L Gates LLP

(57) ABSTRACT

Disclosed are safe, simple and effective broad-spectrum treatments for halitosis and other microbial infections of the nondental upper respiratory tract useful to treat bacterial and other microorganism species, including anaerobic bacteria. Electromagnetic radiative energy including visible, and optionally, thermal, RF and/or microwave wavelengths, is topically applied to internal surfaces of the upper respiratory tract to destroy or incapacitate superficial microorganisms without the use of antibiotics. One useful apparatus is a handheld energy applicator having a light output head suitable for treating the back of the tongue and the tonsils and which may be interchangeably provided with extensions to reach the sinuses. The energy applicator can be supported and guided by a mounting device held between the subject's teeth, if desired. Useful embodiments of the invention include preparative treatment of the target surfaces with a photosensitizing agent such as an oxidizing agent or a complementary stain. Optionally a pre-treament procedure may be employed to remove detritus and microfloral overgrowths that may mask more deeply resident target microorganisms. Novel treatments include treatment of halitosis by destruction of bacterial species associated with halitosis, such as *Atopobium parvulum*, by application of non-ionizing radiative energy to the tonsils and the back of the tongue. Another embodiment comprises a candy bar incorporating a halitosis treatment lamp disposed within the candy.

5 Claims, 6 Drawing Sheets

U.S. PATENT DOCUMENTS

| | | | |
|---|---|---|---|
| 4,736,745 A | 4/1988 | Gluckman | |
| 5,354,293 A | 10/1994 | Beyer et al. | |
| 5,611,793 A | 3/1997 | Wilson et al. | |
| 5,658,148 A * | 8/1997 | Neuberger et al. | 433/215 |
| 6,026,828 A * | 2/2000 | Altshuler | 132/311 |
| 6,086,558 A | 7/2000 | Bower et al. | |
| 6,096,030 A | 8/2000 | Ortiz | |
| 6,159,236 A | 12/2000 | Biel | |
| 6,187,001 B1 | 2/2001 | Azar et al. | |
| 6,214,034 B1 | 4/2001 | Azar | |
| 6,251,127 B1 | 6/2001 | Biel | |
| 6,264,924 B1 | 7/2001 | Witt et al. | |
| 6,290,496 B1 * | 9/2001 | Azar et al. | 433/29 |
| 6,350,435 B1 | 2/2002 | Alvarez Hernandez | |
| 6,364,874 B1 | 4/2002 | Bays et al. | |
| 6,379,376 B1 | 4/2002 | Lubart | |
| 6,409,719 B1 | 6/2002 | Manning | |
| 6,464,625 B2 | 10/2002 | Ganz | |
| 6,471,692 B1 | 10/2002 | Eckhouse et al. | |
| 6,475,172 B1 | 11/2002 | Hall | |
| 6,491,618 B1 | 12/2002 | Ganz | |
| 6,514,243 B1 | 2/2003 | Eckhouse et al. | |
| 6,551,346 B2 | 4/2003 | Crossley | |
| 6,555,093 B2 | 4/2003 | Alvarez Hernandez | |
| 6,558,653 B2 * | 5/2003 | Andersen et al. | 424/49 |
| 6,561,808 B2 * | 5/2003 | Neuberger | 433/215 |
| 6,576,224 B1 | 6/2003 | Osbakken | |
| 6,607,711 B2 | 8/2003 | Pedersen | |
| 6,623,513 B2 | 9/2003 | Biel | |
| 6,702,808 B1 | 3/2004 | Kreindel | |
| 6,902,397 B2 * | 6/2005 | Farrell et al. | 433/29 |
| 7,144,247 B2 * | 12/2006 | Black | 433/29 |
| 2001/0024777 A1 | 9/2001 | Azar et al. | |
| 2002/0061495 A1 * | 5/2002 | Mault | 433/215 |
| 2002/0183808 A1 * | 12/2002 | Biel | 607/88 |
| 2003/0012744 A1 * | 1/2003 | Pedersen | 424/49 |
| 2003/0097122 A1 * | 5/2003 | Ganz et al. | 607/88 |
| 2003/0104340 A1 * | 6/2003 | Clemans | 433/215 |
| 2003/0148393 A1 * | 8/2003 | Woodbury et al. | 435/7.2 |
| 2003/0158544 A1 * | 8/2003 | Slatkine | 606/10 |
| 2004/0019990 A1 * | 2/2004 | Farrell et al. | 15/105 |
| 2004/0022743 A1 * | 2/2004 | Rosenberg Nevo | 424/49 |
| 2004/0224288 A1 * | 11/2004 | Bornstein | 433/224 |

OTHER PUBLICATIONS

D. A. Phoenix et al. "The phototoxicity of phenothiazinium.." FEMS Immunology and Medical Microbiology 39 (2003) p. 17-22.

"Radiancy Received FDA Clearance.." PR Newswire, Jun. 24, 2003, downloaded from http://investor.cnet.com.

Walter J. Loesche et al. "Microbiology and treatment of halitosis", Periodontology 2000, vol. 28, 2002, p. 256-279.

* cited by examiner

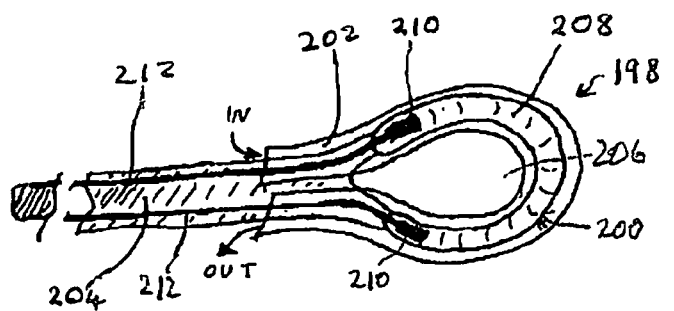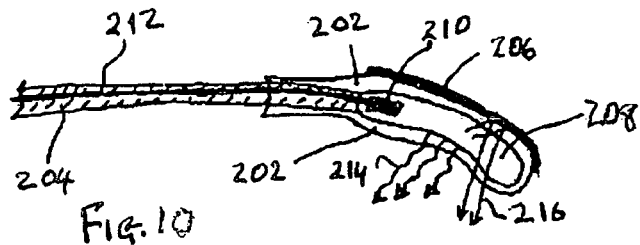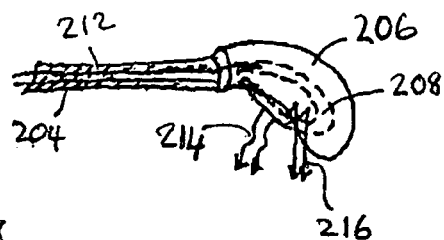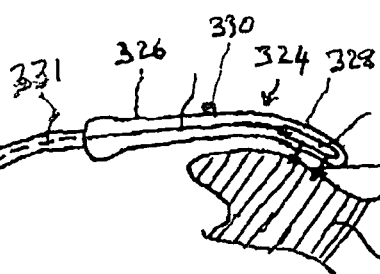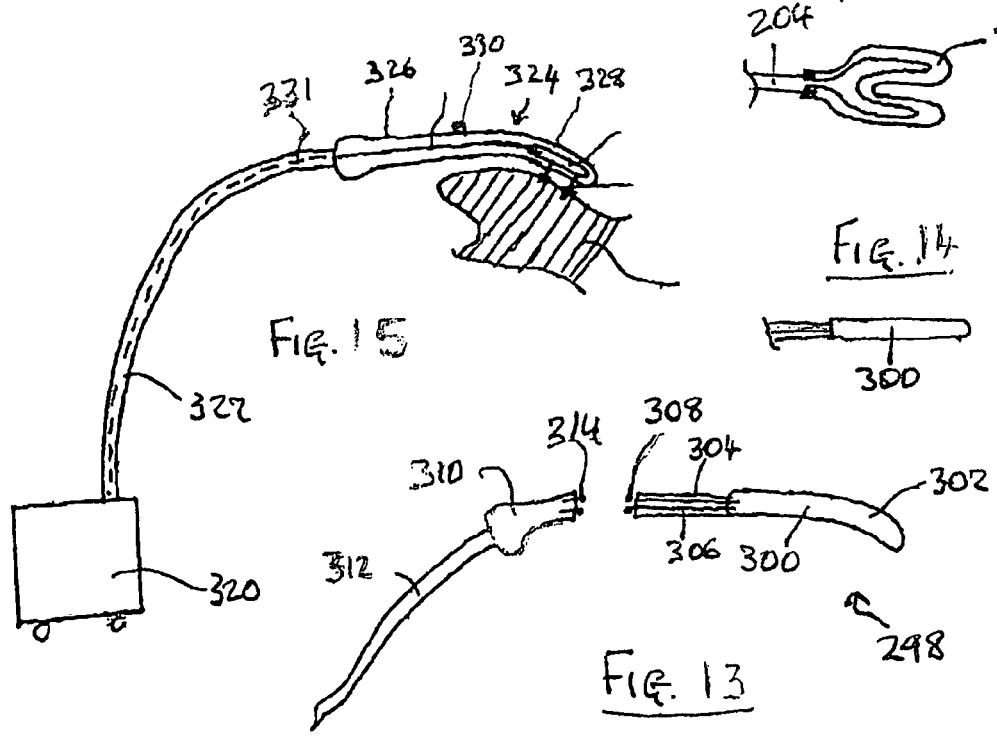

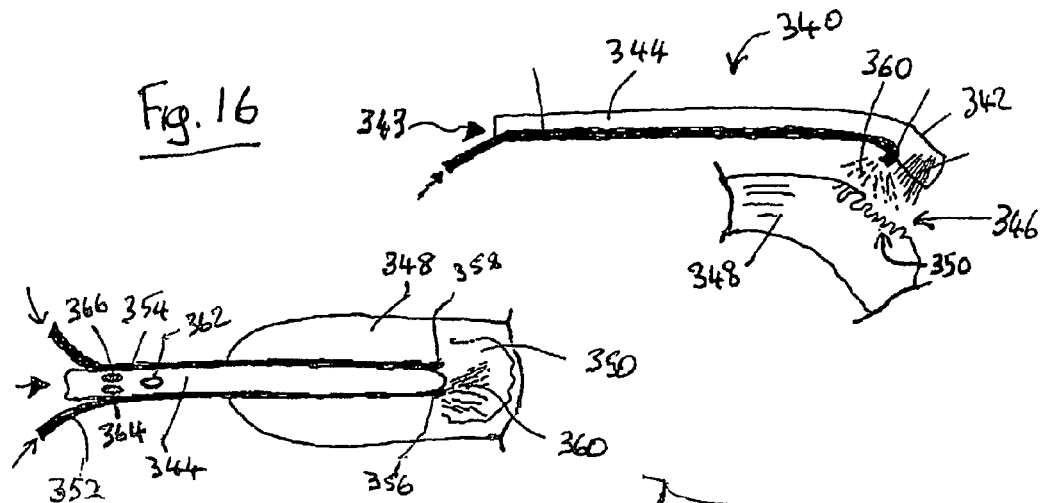
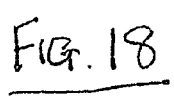
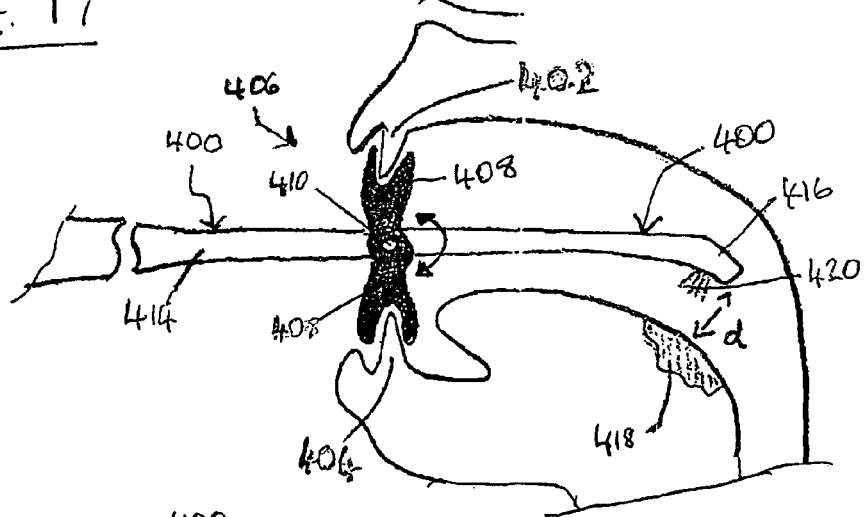
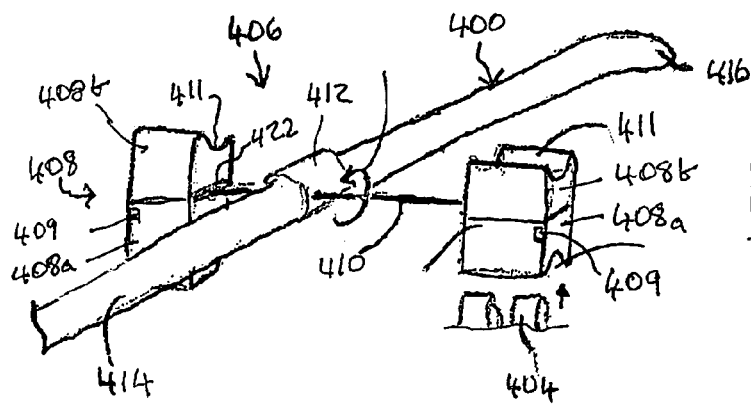

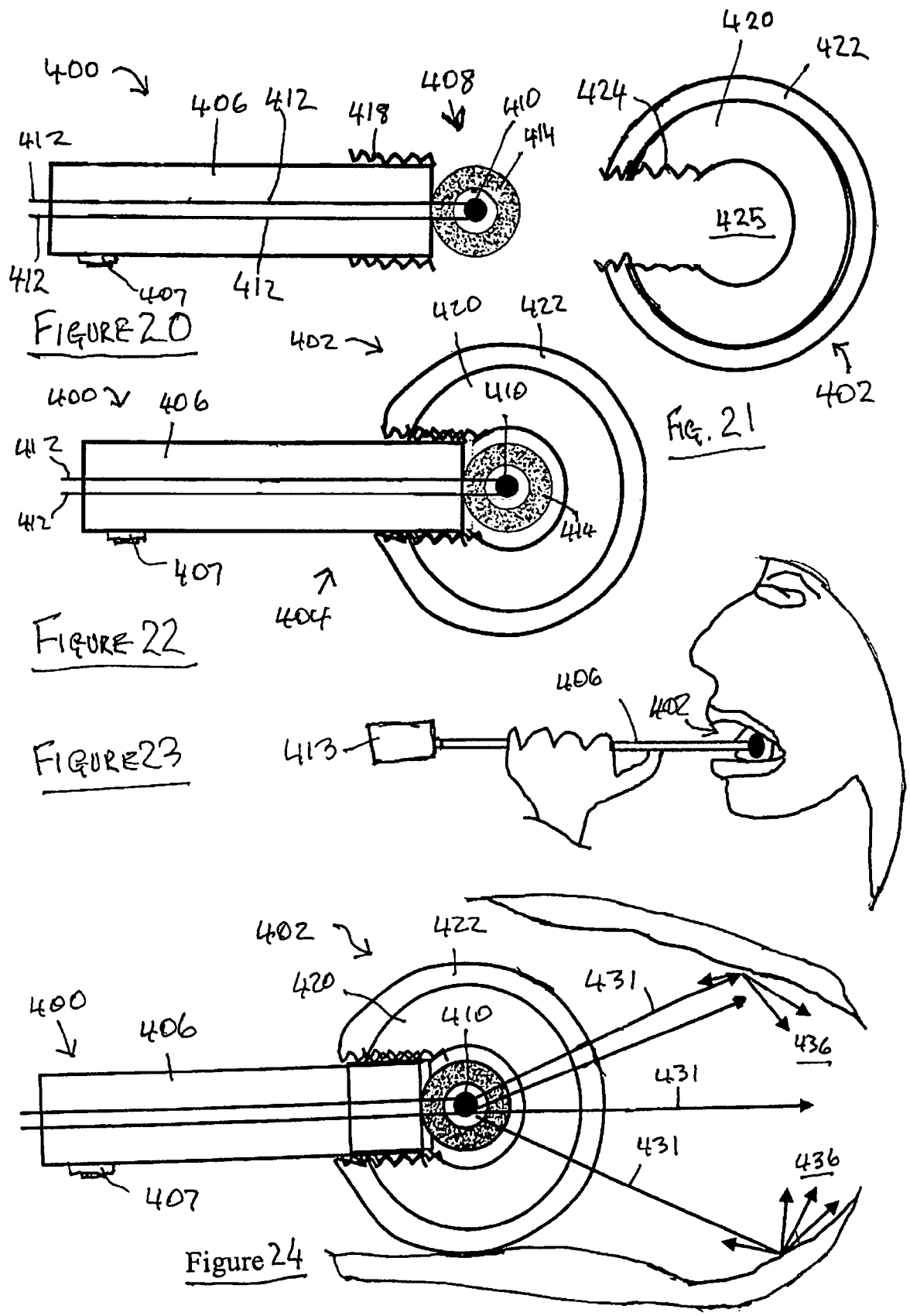

CONTROL OF HALITOSIS-GENERATING AND OTHER MICROORGANISMS IN THE NON-DENTAL UPPER RESPIRATORY TRACT

CROSS-REFERENCE TO RELATED APPLICATIONS

The present application is a continuation of application Ser. No. 10/929,694 filed Aug. 30, 2004 now abandoned which application claims benefit of Krespi et al. provisional patent application No. 60/511,549 filed Oct. 15, 2003. The subject matter of this application is related to that of Krespi et al. copending application Ser. No. 10/929,696 filed Aug. 30, 2004 and entitled "CONTROL OF RHINOSINUSITIS-RELATED, AND OTHER MICROORGANISMS IN THE SINO-NASAL TRACT". The entire disclosure of each one of the aforesaid applications is hereby incorporated herein by this specific reference thereto.

STATEMENT REGARDING FEDERALLY SPONSORED RESEARCH OR DEVELOPMENT (Not applicable.)

BACKGROUND OF THE INVENTION

The present invention relates to methods of treatment and instruments for the control of halitosis-generating and other microorganisms in the non-dental upper respiratory tract. More particularly the methods and instruments of the invention are useful for the control of chronic or low-level infections of bacteria or other microorganisms causing halitosis, sinusitis and other chronic conditions. Many people suffer persistent chronic halitosis, being bad or malodorous breath, which can often be diagnosed as being attributable to resilient colonies of bacteria that have become established in posterior oral locations such as the back of the tongue and the tonsils. As is well known, the affliction of halitosis (bad breath) may constitute a serious problem, particularly in social situations. Halitosis can be quite severe and it may occur occasionally or chronically or regularly, for example at specific times of the day or month.

Studies on the etiologies of breath malodor indicate that volatile sulfur compounds ("VSCs") which have unpleasant odors, even in extremely low concentrations, are the principal odorants in bad breath. Some examples of such VSCs are hydrogen sulfide, mercaptans, methyl mercaptan, dimethyl sulfides, skatole, cadaverine, putrescine and isovaleric acid. Such volatile sulfur compounds may originate from the anaerobic bacterial degradation, notably by anaerobic Gram-negative bacteria, of sulfur-containing amino acids within the oral cavity. However, the bacteria responsible for halitosis have not as yet been fully elucidated.

As described by C. E. Kazor et al. in "*Diversity of Bacterial Populations on the Tongue Dorsa of Patients with Halitosis and Healthy Patients*" Journal of Clinical Microbiology, February 2003, p. 588-563, the oral cavity of normal, healthy humans i bacterial species. These bacteria form a unique ecosystem with complex interactions and interdependencies between species with some bacteria producing substrates consumed by other bacteria. Environmental factors, such as diet or decrease of host immune resistance may lead to the overgrowth of unfavorable species for example *Porphyromonas gingivalis, Prevotella intermedia, Fusobacterium nucleatum, Treponema denticola, Actinobacillus actinomycetemcomitans* and *Bacteroides* spp whose presence as significant populations may be associated with health disorders or disease conditions.

Some such conditions include chronic periodontitis, that is a major cause of tooth loss in adults when unfavorable species inhabit the periodontal pockets and halitosis (or bad breath) associated with the presence of unfavorable species on the back and base of the tongue. Conventionally, antibiotics are used to treat offending bacteria associated with conditions sufficiently severe to be inflammatory. Nevertheless, in chronic bacterially induced conditions there may be severe disadvantages to the long-term use of pharmacological antimicrobial agents, either systemically or topically. Possible drawbacks include the development of resistance rendering the agents clinically ineffective and disruption of the normal oral microflora present in healthy individuals. Gastrointestinal disturbances may also be associated with use of antibiotics.

As described by Wilson et al. in Int. Dent. J. 44:181-189, many therapeutic regimens used for oral infections eliminate both pathogenic and commensal organisms indiscriminately, thereby disrupting the natural ecosystem of the oral cavity. According to Kazor et al., certain bacterial species are significantly associated with halitosis for example *Atopobium parvulum, Eubacterium sulci, Fusobacterium periodonticum*, a phylotype (clone BS095) of *Dialister*, a phylotype (clone BW009) of *Streptococcus*, a phylotype (clone DR034) of the uncultivated phylum TM7 (8), and *Solobacterium moorei*. (See FIG. 1 and Table 2.) Some other species that have been associated with halitosis include *Porphyromonas gingivalis, Fusobacterium nucleatum, Bacteroidesforsythus, Treponema denticola, Actinobacillus actinomycetemcomitan* and *Prevotella intermedia*.

Some species are also described as being associated with good health for example *Streptococcus salivarius, Rothia mucilaginosa (Stomatocossus mucilaginosus)*, and an uncharacterized, cultivable species of *Eubecterium* (strain FTB41) (See FIG. 1 and Table 2). In contrast, *S. salivarius* was reportedly detected in only one of the subjects with halitosis and was detected at very low levels.

There exists a large market for mouthwashes, mouth rinses, dentifrices, chewable, gums and the like and other dental application products for oral hygiene use many or most of which are intended to control halitosis and which have varying degrees of effectiveness.

Antiseptic materials such as chlorhexidine, cetylpyridinium chloride, benzalkonium chloride, thymol eucalyptol, methyl salicylate, benzoic acid, boric acid, menthol, sanguinarine chloride and others are intended to control the formation of bacterial plaque. Antibiotics, such for example as metronidazole may also be employed. Herbal treatments for halitosis, including parsley, mint or olive oils or the like, have also been proposed. See for example Alvarez Hernandez U.S. Pat. Nos. 6,555,093 and 6,350,435.

For example, Ratcliff U.S. Pat. No. 4,689,215 discloses a treatment for halitosis wherein the oral cavity is rinsed with an aqueous solution of what is known as "stabilized chlorine dioxide", a substance which provides a source of sodium chlorite, a precursor to chlorine dioxide which may be active against causative bacteria.

More recently, Witt, et al. U.S. Pat. No. 6,264,924 disclose use of a chewing gum containing small amounts of chlorite ion for antimicrobial and tooth whitening effects.

Also, for example, as disclosed in Pedersen U.S. Pat. No. 6,607,711, it has been proposed to employ chelated zinc in oral hygiene compositions intended to control halitosis.

Notwithstanding a wide range of available remedies such as the foregoing, it has been estimated that as many as 20-90 million people in the United States continue to be afflicted with the embarrassment and distress of halitosis, possibly because of the failure of such remedies to be fully effective. Pursuant to the present invention, it can be understood that such ineffectiveness may be attributable to the transient presence of the remedies in the vicinity of the bacteria, to the failure of the topically applied treatments to penetrate tissue surfaces and to biochemical resistance to the applied treatments and to the need for continual repetition of the treatments.

Some proposals for halitosis treatment recognize and address bacterial infection of the tonsils as a causative agent. For example, Hall U.S. Pat. No. 6,475,172 discloses a tonsil cleansing tool for removing food debris from a tonsillar pit by applying pressure to a surface of the tonsil close to the debris.

As described by Hall, human tonsils comprise a number of small lymphoid tissue organs located in a ring around the pharynx where they protect the entrance to the throat, namely the two palatine tonsils on each side of the tongue, the lingual tonsil at the back of the tongue and the pharyngeal tonsils, or adenoids, at the back of the pharynx. The tonsils are generally almond shaped and spongy textured, having small pits or cavities at their surfaces which are intended to collect invading microorganisms but which may also collect and harbor small food particles and sinus drainage and other debris which materials provide a substrate for microbial colonization and proliferation. Anaerobic bacteria generating malodorous VSCs can readily become established in these favorable locations, providing persistent sources of bad breath that are difficult to control or eradicate.

The tonsils are accordingly of particular interest as treatment targets for the processes of the invention in cases of halitosis. The tonsils are locations that may harbor persistent colonies of anaerobic bacteria and other microorganisms. Prescription of systemic antibiotics may be deemed unwise for a condition not regarded as presenting substantive risk of developing more serious pathologies or, if acceptable, may provide only short term control, with the unpleasant symptoms again presenting themselves within a few weeks or months of the initial relief. Alternatively, the bacterial colonies may be, or become resistant and antibiotics may have little if any effect. Use of antibiotics may eliminate susceptible strains providing opportunities for resistant strains to proliferate.

Orally administered topical agents, mouthwashes and the like may bring too little active agent to the site of infection for too short a period to be wholly effective. Neither systemic nor topical antibiotics are likely to be effective against viral or fungal infections which may be present as predominant or component microorganisms in the infection. Comparable considerations may apply to other infections of the nondental upper respiratory tract, such as nasal and sinus mucous tissues or cavities, for which there are ongoing needs for more effective simple treatments.

Various methods are also known for the treatment of bodily infections on internal surfaces which employ radiant energy as an alternative to antibiotic or chemical agents.

For example, Ganz U.S. Pat. Nos. 6,491,618 and 6,464,625 disclose methods and apparatus employing ionizing radiation, for example, ultraviolet light or x-ray radiation for treating gastrointestinal ailments of a patient including gastritis, gastric ulcer, duodenal ulcer, gastric cancer, gastric lymphoma, ulcerative colitis, or Crohn's disease. Such treatments are usually quite drastic and may not be suitable for treatment of chronic oral conditions. Tissue damage and inflammation as well as destruction of desirable commensal microbiotic species, may be induced by long-term application of such treatments. Furthermore, employment of short wavelength radiation risks DNA damage and possible carcinogenicity.

Other radiative treatments that have been employed for treating human microbiotic infections include photodynamic therapy. Photodynamic therapy is a relatively recent treatment method whose primariy applications have employed laser light to destroy tumor cells. The laser energy is targeted to the pathologic cells by staining the cells with specific dyes that have energy absorption peaks overlapping the laser energy wavelength whereby tumor cells absorb more laser energy than normal cells.

For example, Biel U.S. Pat. No. 6,159,236 discloses a medical device including a tube and expandable member which emits light for photodynamic therapy to treat internal body surfaces such as the larynx or cheek in order to treat or detect pathologies such as cancer and microbiological pathogens. An integrated array of vertical cavity surface emitting lasers (VCSEL) can provide a light emitting source for photodynamic therapy ("PDT") treatment. Light is transmitted through an expandable member or balloon, which is inflated by air or a fluid, possibly a proteinaceous light-diffusing gel. The expandable member conforms with the surface to be treated.

Azar et al. United States Patent Application 20010024777 discloses another radiative energy treatment employing a toothbrush-like apparatus for self use to effect photothermolysis of oral plaque bacteria sensitized by staining. The apparatus functions to direct light on to at least one tooth. In order to avoid coagulation of blood vessels, light wavelengths near oxyhemoglobin absorption peaks are avoided, e.g. by filtration of the applied energy. Other biomedical applications of photothermal energy include external topical application especially for depilation, hair removal, for example, as disclosed in Azar and Shalev U.S. Pat. No. 6,187,001 and Azar U.S. Pat. No. 6,214,034. Kreindel U.S. Pat. No. 6,702,808 discloses use of light in combination with RF energy for treating hair, vascular lesions and other complex targets on the skin.

It is also known that electromagnetic radiation can be employed to destroy different types of bacteria, for example, Phoenix et al. in "*The Phototoxicity Of Phenothiazinium Derivatives Against Escherichia Coli And Staphylococcus Aureus*" FEMS Immunol Med Microbiol. 2003 Oct. 24; 39(1): 17-22 teach that phenothiazinium derivatives like methylene blue and toluidine blue O can cause bacterial cell death in both gram negative (*E. Coli*) and gram positive (*Staph aureus*) bacteria by phototoxicity when employed at "micromolar concentrations, levels much lower than those used in the topical and intravenous administration of a number of phenothiazinium compounds". Illumination is effected by placing microtiter plates in a light box. Phoenix et al. suggest the tested dyes could be "useful in the phototherapy of localised bacterial infections, burn injuries for example."

Animal studies have also been used to suggest human treatments. Teichert et al., in "*Treatment of oral candidiasis with methylene blue-mediated photodynamic therapy in an immunodeficient murine model.*" Oral Surg Oral Med Oral Pathol Oral Radiol Endod. 2002 February; 93(2): 155-60, described evaluating the efficacy in an immune-compromised murine model of using methylene blue-mediated photodynamic therapy. This is a narrow-focus treatment of a single target fungal organism, oral candidiasis, a pathogen commonly afflicting immune-compromised AIDS patients. The authors reported that methylene blue concentrations of 450 and 500 microgram/mL activated with diode laser light at 664 nm using a cylindrical diffuser at 275 J/cm fiber length at 400 mW for 687.5 seconds, were able to "totally eradicate" *Candida albicans* in an immunosuppressed murine model. Teichert et al. professed to be the first to use antimicrobial photodynamic therapy "PDT" in an animal model and to treat oral candiasis by using a methylene blue-mediated photodynamic therapy. Teichert et al. suggests methylene blue-mediated PDT of oral candidiasis as a potential treatment alternative to traditional antifungal drug therapy.

Teichert et al.'s teachings regarding the response of a single fungal species in abnormal, immune-compromised mice do not suggest a solution to the problem of providing a treatment that can be directed against a broad-spectrum of bacterial populations in diversified members of the human population most of whom may have normal immunity. Furthermore, Teichert et al.'s treatment is time-consuming having a duration of 687.5 seconds (page 156, right hand column), about 11.5 minutes, and is intended to be applied only to a specific acute care patient group, AIDS patients, rather than to segments of the population that may largely be in moderate to good health.

Wilson et al. U.S. Pat. No. 5,611,793 discloses use of laser light in combination with a photosensitizing agent to disinfect or sterilize oral cavity tissues, wounds or lesions. Wilson's disclosed uses are dental or dentally related and include disinfecting and sterilizing dental tissues, gingival tissues and drilled-out carious lesions prior to filling, destroying cariogenic microbes on a tooth surface, treatment or prevention of chronic periodontitis and inflammatory periodontal diseases; treating oral candidiasis in AIDS patients, immuno-compromised patients and patients with denture stomatitis. Nondental applications are not suggested.

None of the foregoing proposals describes a simple and safe, non-chemical, broad-spectrum treatment of upper respiratory tract infections, including halitosis, in diverse human populations largely comprising otherwise healthy individuals, and which is suitable for repeated application to treat chronic conditions. Furthermore, many, if not all, known treatments act largely superficially and may fail to reach organisms lodged more deeply beneath the epithelial surface.

Accordingly, there is a general need for simple, more effective treatments of infections of nondental upper respiratory mucous tissues and specific needs for improved treatments of halitosis, sinus and nasal infections, for treatments which will be effective against Gram-negative bacteria and for deep treatments that can penetrate to organisms harbored beneath exposed surfaces.

The foregoing description of background art may include insights, discoveries, understandings or disclosures, or associations together of disclosures, that were not known to the relevant art prior to the present invention but which were provided by the invention. Some such contributions of the invention may have been specifically pointed out herein, whereas other such contributions of the invention will be apparent from their context. Merely because a document may have been cited here, no admission is made that the field of the document, which may be quite different from that of the invention, is analogous to the field or fields of the present invention.

BRIEF SUMMARY OF THE INVENTION

The present invention provides, in one aspect, a method of controlling microorganisms infecting the nondental upper respiratory tract comprising applying electomagnetic energy to infected mucous tissues at a target site the nondental upper respiratory tract in a manner effective to obtain a desired control of the microorganisms wherein the electromagnetic energy is pulsed and comprises light and optionally longer wavelength energy.

If employed, the longer wavelength energy can, for example, comprise radiant heat, RF or microwave energy, combinations of two or more of same, or other suitable energy flux.

The electromagnetic energy desirably is chosen to be suitable for repeated use over weeks or months to treat chronic tonsillar, rhinal, sinal and other respiratory tract infections without inducing significant pain, discomfort or inflammation. Desirably the energy treatment should permit survival of significant proportions of commensal microorganisms. To these ends, the electromagnetic energy is preferably nonionizing and includes one or more energy peaks in the visible spectrum. The electromagnetic energy can comprise laser energy with a characteristic frequency in the visible or near-infrared spectrum pulses of photothermal energy rich in blue light wherein at least 70 percent of the pulse energy in the visible spectrum is polychromatic and is contained in a blue-green waveband of from about 400 to about 600 nm or from about 400 to about 500 nm.

Alternatively the electromagnetic energy can comprises pulses of photothermal energy wherein the light energy in the visible spectrum is orange or red. Individual treatments can comprise separate applications of one or more pulses of such blue or blue-green light and such orange or red light. The electromagnetic energy can have a pulse width of not more than about 200 msec and an interval between pulses of from about 10 to about 2000 msec.

The energy application can be performed from one to five times per week for a period of from about two to about sixteen weeks and can be controlled to apply sufficient photothermal energy to effect a microorganism count reduction of at least about 80 percent. In one embodiment the energy application is effected to raise the temperature of the target tissue to from about 50° C. to about 70° C.

In another aspect, the invention provides a method for the treatment of halitosis comprising applying light energy to a tonsillar or lingual location determined to harbor a colony of microorganisms generating malodorous gas at a wavelength and intensity and for a duration effective to control the colony of microorganisms.

The invention also provides, in a further aspect, a method and apparatus for non-ablative treatment of lingual, palatine or other tonsils, and/or other pharyngeal anatomy wherein the treatment comprises delivering optical energy to the tonsils ot other anatomy in an amount which reduces the gram negative bacterial burden of the tonsils below a level which can produce sulfuric compounds at a desired level for example 200 ppb, 80 ppb or other suitable level as known or apparent to those skilled in the art in light of this disclosure.

To facilitate treatment of deeply lodged organisms located beneath tissues surfaces, the invention can include a pretreatment procedure comprising removal of superficial microflora or other detritus or both, which optionally may include a mild exfoliation of one or more outer epithelial layers.

In a still further aspect, the invention provides treatment instrument useful for the treatment of a person suffering from halitosis comprising:

a) a handle gripped in proximity to the person;
 b) a light output head stably supported on the handle and positioned in the person's posterior oral cavity or pharynx in a location juxtaposed to a tonsil or the back of the tongue to output light to the tonsil or the back of the tongue; and
 c) a light source to provide light for output from the light output head;

wherein the treatment instrument can be actuated to apply light from the light source to the tonsil or the back of the tongue.

In another aspect, the invention provides a candied photoapplicator for delivering light to treat microorganisms populating a target site in the oral-pharyngeal cavity, the candied photoapplicator comprising:
a) an illuminator member;
b) a light source supported on the illuminator member to illuminate the target site in the oral cavity; and
c) a candy component supported by the illuminator member, the candy component being suitable for sucking by the subject while the illuminator member illuminates the oral cavity. Such a candied photoapplicator embodiment provides an appealing device or means for self-treatment and is particularly suitable for children. Steps can be taken, as described hereinbelow, and as will otherwise be apparent to those skilled in the art to effectively protect the source of illumination and to facilitate safe and effective operation of the photoapplicator.

The methods and instruments of the invention provide novel, simple effective treatments for chronic halitosis, sinusitis and other low-level infections of the nondental upper respiratory tract which can quickly and easily be carried out in a doctor's or dentist's office by a physician, dentist or other qualified practitioner, or could be effected by consumers. Systemic or topical drugs are not required and accordingly problems of antibiotic resistance are avoided. Nor is it necessary to employ damaging radiation, such as ionizing radiation which might induce long-term adverse effects attributable to mutagenicity, carcinogenicity or teratogenicity.

BRIEF DESCRIPTION OF THE SEVERAL VIEWS OF THE DRAWING

Some embodiments of the invention, and of making and using the invention, as well as the best mode contemplated of carrying out the invention, are described in detail below, by way of example, with reference to the accompanying drawings, in which like reference characters designate like elements throughout the several views, and in which:

FIG. 9 is a plan view, partly in section, of a photothermal treatment device employing a distally mounted flash lamp;

FIG. 10 is a side elevation view of the photothermal treatment device of FIG. 9;

FIG. 11 is a side elevation view of another embodiment of photothermal treatment device according to the invention;

FIG. 12 is a plan view of a flash lamp configuration suitable for use in the photothermal treatment device illustrated in FIGS. 6-8;

FIG. 13 illustrates a further embodiment of photothermal treatment device according to the invention having a detachable treatment head;

FIG. 14 is a plan view of the detachable head illustrated in FIG. 13;

FIG. 15 schematically illustrates a photothermal treatment device system according to the invention employed for treating the back of the tongue;

FIG. 16 illustrates a combination photothermal bacterial treatment system according to the invention employed for treating the back of the tongue which device includes a fluid applicator for a bacterial sensitizing or other fluid;

FIG. 17 is a plan view of the device of FIG. 16 with more of the tonguei illustrated;

FIG. 18 illustrates the use of a photothermal treatment apparatus according to the invention to treat the tonsillar region of the posterior oral cavity, the apparatus comprising a photothermal applicator and a dentally secured mounting device to assist the photothermal application procedure;

FIG. 19 is a front perspective view of the mounting device shown in FIG. 18;

FIG. 20 is a plan view in section of an illuminator bar being one component of a candied photoapplicator embodiment of the invention;

FIG. 21 is a plan view in section of a hollow candy being another component of the photoapplicator shown in FIG. 20;

FIG. 22 is a plan view of a candied photoapplicator embodiment of the invention comprising the illuminator bar component shown in FIG. 20 assembled with the hollow candy component shown in FIG. 22;

FIG. 23 illustrates the candied photoapplicator shown in FIG. 22 in use as it is being inserted into the oral cavity of a subject; and FIG. 24 is schematic view of the candied photoapplicator shown in FIG. 22 as it might be deployed within the oral cavity to deliver light and optionally, treatment agents to adjacent tissues.

DETAILED DESCRIPTION OF THE INVENTION

The following more detailed description of the invention is intended to be read in the light of, and in context with, the preceding summary and background descriptions but without being limited by the preceding descriptions.

In one aspect the invention provides a method of treating low-level infections in the nondental cavities or regions of the upper respiratory tract, the method comprising application to target tissue in the nondental upper respiratory tract of sufficient photothermal energy to effect a colony microorganism count reduction of at least about 50 percent. Some useful embodiments of the invention effect a microorganism count reduction of at least about 80 percent, or at least about 90 percent and such a reduction can be effected in a single treatment. The treatments may be repeated, as necessary, to control the microorganism population.

Some useful embodiments of the invention include a mechanical, chemical or other pre-treatment procedure to remove superficial microflora or other detritus or both, and to facilitate or enhance exposure of more deeply lodged organisms located beneath tissue surfaces to the electromagnetic radiation and other agents employed in the primary treatments of the invention. Desirably, the pre-treatment is performed shortly before the primary treatment.

To achieve a desired reduction in microorganism count, the treatment energy can be applied in a dosage which is a multiple of the $LD_{50}$ for a target organism, for example, a multiple in the range of about 1 to about 3 times the $LD_{50}$, for example about two times the $LD_{50}$ which will provide a reduction of 90 percent.

The photothermal energy can be produced in any suitable manner, for example by operating a flashlamp to generate a pulsed electromagnetic output comprising both visible light and thermal energy. The energy pulse or pulses produced, or flashes, can be directed to a desired target surface in any suitable manner, for example by reflecting the energy through a window in a housing. The angular divergence of the pulses can be controlled to control the depth of penetration into mucous target tissue, if desired, with wider beams penetrating less deeply, for example by suitable choice of the shape of the reflector and other light guiding surfaces between the source and the target site.

Figure 1:
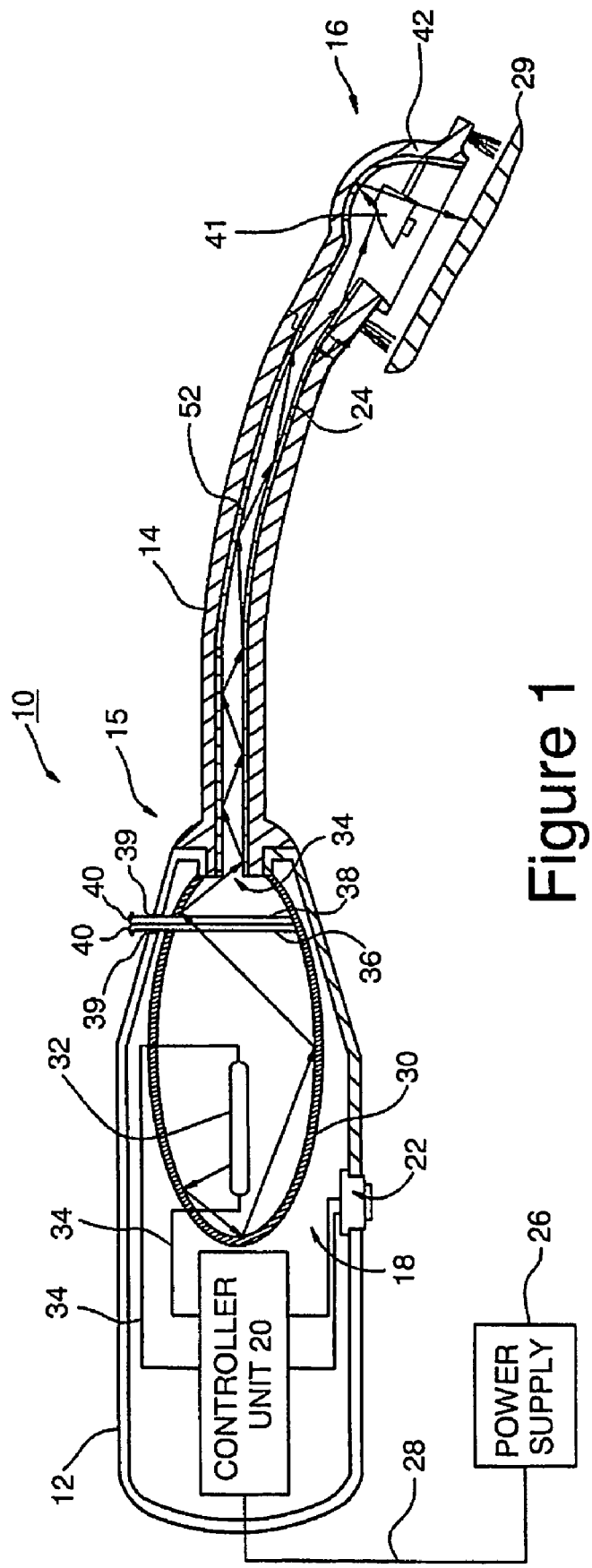
FIG. 1 is a sectional and partially schematic view of a photothermal treatment instrument according to one embodiment of the invention suitable for treating the posterior oral cavity.
Figure 2:
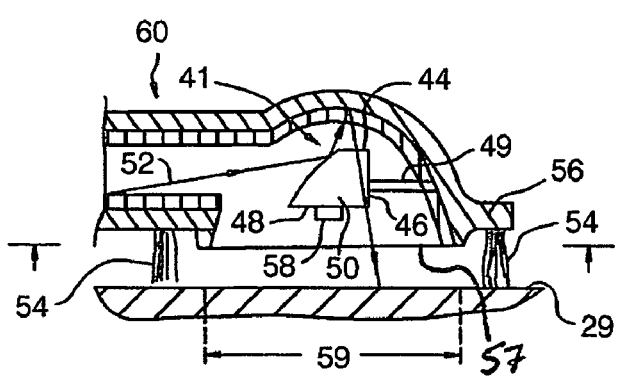
FIG. 2 is an enlarged view of a light output head being a component of the photothermal treatment instrument shown in FIG. 1.
Figure 3:
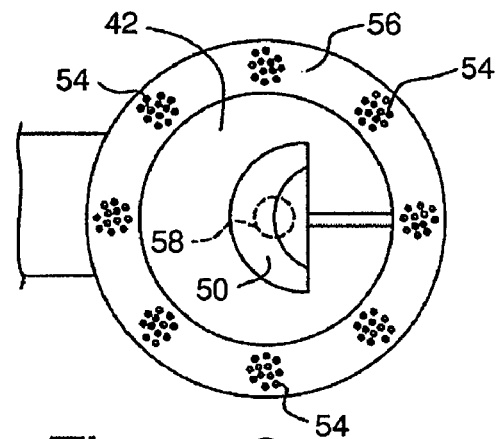
FIG. 3 is a view on the line 3-3 of FIG. 2.

Referring to FIGS. 1-3 of the drawings, the photothermal treatment instrument 10 there illustrated is designed to be held and operated in one hand, either the left or the right hand and comprises a partially tapered, generally cylindrical body 12, serving as a handle, from which projects, in the axial direction an elongated neck 14 carrying an output head 16. As shown, neck 14 can curve or bend away from the axis of cylindrical body 12 to facilitate treatment of the posterior oral cavity.

With advantage, neck 14 can be releasably attached to body 12 by a joint 15 which can be a push or screw fit or other suitable connection. Neck 14 stably supports light output head 16 on body 12, maintaining light output head 16 in a desired position above body 12 when body 12 is gripped and held upright. Thus, light output head 16 can be carefully positioned in relation to a target site by gripping and manipulating body 12 with one hand and photothermal treatment instrument 10 is suitable for treating posterior oral and other surfaces.

Cylindrical body 12 houses a light source 18 and controller unit 20 for light source 18 operated by an on-off switch 22. Neck 14 is traversed by a light pipe 24 which guides light from light source 18 to output head 16. As shown, light source 18 is powered from an external power supply 26, via a power cord 28. However, it will be understood that rechargeable or other batteries (not shown) can be housed in body 12, if desired, as either a supplement to or an alternative to external power supply 26.

Body 12 of photothermal treatment instrument 10 can be comfortably gripped in one hand and switch 22 can be operated to activate light source 18 via controller unit 20. Light source 18, when activated, generates light and heat which are transmitted along light guide 24 through neck 14 to be output from output head 16 on to a treatment target site 29, as will be described in more detail hereinbelow. Body 12, except as may otherwise be apparent herein, can have any suitable cross-section for example, circular, but other cross-sectional shapes, such as oval, rectangular or polygonal that can conveniently be accommodated in a user's hand, may be employed if desired.

As may be understood from FIG. 1, body 12 and its internally accommodated light-generating components can be constructed in a generally similar manner to housing 12 and the light-generating components housed therein disclosed in Azar et al. Pub. No. US 2001/0024777, particularly in FIG. 3 and at paragraphs [0075] to [0080] the entire disclosure of which patent publication is hereby incorporated herein by reference thereto. However, in the currently described embodiments of the present invention, the energy delivered, the light delivery system and the target sites are or can be quite different from Azar's intended destruction of sensitized plaque bacteria on the teeth.

Incoherent light source 18 in body 12 can include a lamp reflector 30 and a lamp 32 disposed within reflector 30. Lamp 32 is electrically connected to controller unit 20 via leads 34 and is powered from power supply 26 in response to actuation of switch 22 under the control of controller unit 20. If desired, lamp 32, and optionally also, reflector 30 can be user removable and replaceable in body 12 to enable the user to replace lamp 32 with a lamp having different energy output characteristics during a treatment procedure. For this purpose, body 12 may have an access opening and cover therefor (neither one shown).

Lamp reflector 30 can have any suitable shape to collect light from lamp 32 and reflect the collected light into light pipe 24, via a proximal opening 34, for example, ellipsoidal, quasi-ellipsoidal, parabolic, quasi-parabolic, spherical, quasi spherical and the like.

If desired, one or more filters, such as are shown at 36 and 38, can be provided in the light path between lamp 32 and proximal opening 34 to limit the spectrum of the output light. Preferably, filters 36, 38 are selectively removable from body 12, for example through slots 39 by grasping tabs 40 which project externally of body 12, to enable a user to select desired filtration characteristics. Filters 36, 38 and any other optical components in the light path from lamp 32 to target site 29 are preferably heat-transmissive to permit heat from lamp 32 to be applied to the target site 29 along with light duly filtered, if desired. By inserting or removing one or more of filters 34, 36, a user may vary the filtration, for example, between zero filtration and a high degree of filtration provided by a low bandpass and a high bandpass filter with adjacent cutoff frequencies which provide an output with a particularly narrow waveband, if desired. Some useful frequency ranges such as blue, blue-green or orange with or without limited ultraviolet, are described hereinbelow.

Suitable filters 34 and/or 36, or possibly even three filters, that can be employed to provide desired outputs, as described herein, will be apparent to those skilled in the art. If desired, without limitation, filters 34, 36 may comprise: a single blue filter, for example a filter having a transmission spectrum wherein at least about 90 percent of the energy lies between about 400 to about 500 nm; a single blue-green filter, for example a filter having a transmission spectrum wherein at least about 90 percent of the energy lies between about 400 to about 600 nm; an orange filter transmitting at least about 70 percent of the incident infrared energy, which may optionally transmit at least about 90 percent of the energy at wavelengths of about 600 nm and longer; or an ultraviolet filter transmitting no more than 10 percent of incident UVC, and optionally, no more than about 40 percent of incident UVA and UVB.

Alternatively, the ultraviolet filter may transmit no more than about 10 percent of incident UVA, UVB and UVC radiation. In other embodiments of the invention, filters, 34, 36 can comprise an ultraviolet filter as described and one of the blue, blue-green or orange filters, as described.

Lamp 32 can be any suitable lamp providing an incoherent broadband light output of with an appropriate energy-versus-wavelength output spectrum for the purposes of the invention. Lamp 32 may for example be an arc discharge lamp, a flash lamp, such as a xenon or quartz xenon flash lamp, or other suitable lamp and may have a peak energy output around 500 nm or at other suitable wavelength. Such a lamp will generally deliver heat energy as well as light. For treatments limited to blue-rich light, other light sources may be employed for lamp 32, including sources delivering little or no heat energy and having peak energy outputs at shorter wavelengths.

As indicated above, photothermal treatment instrument 10 can be designed for lamp 32 to be readily changed by a user. In this case, photothermal treatment instrument 10 can include multiple lamps 32 having different output characteristics enabling the user to vary the energy output during a treatment procedure. The outputs can be comparable with or equivalents of the outputs obtainable with filters 34, 36 and may be suitably modified with filters, if desired. It will be understood that a suitable filter or filters can be selected for use with a particular lamp and changed when the lamp is changed, if desired.

Lamp 32, when utilized in photothermal treatment instrument 10 can be such as to provide an output capable of photothermolysis of unstained bacteria, and other microorganisms resident on or populating mucous tissues in the nondental upper respiratory tract, preferably without significant tissue damage. It will be understood though not required by the present invention that staining of the microorganisms may be employed if desired. However, many embodiments can be effected without this undesirable and unesthetic complication.

Controller unit 20 includes suitable circuitry to operate flash lamp 32 with desired pulse characteristics, as will be described. The circuitry (not shown) can include a triggering unit, a capacitor unit and electronic timing circuitry for timing the flash frequency.

Neck 14 can be curved or angled, along its length, about an axis transverse to its length, as illustrated, so that photothermal treatment instrument 10 can be inserted in the oral cavity with output head 16 suitably juxtaposed to a treatment surface in the posterior oral cavity and with body 12 downwardly out of the physician's line of sight to the target tissues. The length of neck 14 is sufficient for this purpose. Light pipe 24 can be a reflectively lined tubular passage, fiber optic or other suitable light-conveyance device and neck 14 can be formed of a suitable structural material, preferably a heat- and light-insulating material.

Output head 16. In the embodiment of the invention shown in FIGS. 1-3, output head 16 is designed to spread light received from light pipe 24 and to redirect the received beam in a controlled manner in a direction transverse to the light pipe.

In this embodiment, output head 16 comprises a convex-surfaced deflector 41 which deflects and spreads light received from light pipe 24 and a concave reflector hood 42 which collects light received from deflector 41 and light pipe 24 and outputs the collected light toward target site 29. Reflector hood 42 can collimate the light to a desired degree, for example to provide a light output beam which has a modest divergency, for example a divergence of from about 5° to about 20°, referring to the angle made by the outer periphery of the light beam to the beam axis. The divergency of the output light beam can be controlled by selection of the curvature and shape of reflector hood 42 as known to those skilled in the optical arts. Alternatively reflector hood 42 could be shaped and dimensioned to provide a generally parallel, fully collimated output beam, if desired.

Reflector hood 42 can have any suitable shape that will provide a desired output beam including, for example, one of the shapes described for lamp reflector 30. In particular, a parabolic or quasi-parabolic shape may be employed with the focus of the parabola positioned to promote a desired degree of output beam divergence.

A purpose of deflector 41 is to spread light around reflector hood 42, in some cases with multiple reflections off deflector 41, to reduce variations in intensity of the output beam on the target surface within the target area. Deflector 41, as shown, has the shape of a truncated quarter sphere with flat upper, distal and lower faces 44, 46 and 48 respectively, referring to the orientation of output head 16 in FIG. 2. Deflector 41 is supported from reflector hood 42 by a support strut 49 extending from distal face 48.

Deflector 41 presents a convexly curved surface 50 to light emanating from light pipe 24. In the embodiment shown, curved surface 50 is spherically curved with a radius chosen to distribute light approximately uniformly on the first surfaces of reflector hood 42 that are struck by light after reflection from deflector 41.

As shown in FIG. 3, the curvature of deflector 41 extends laterally in the plane parallel to the surface of the target site 29 so as to deflect light in directions around reflector hood 42, in the transverse plane shown in FIG. 3, where deflector 41 has a semicircular shape. Deflector 41 can have a diameter in this plane which is approximately equal to the width of light pipe 24. The cutoff provided by upper face 44 permits a portion of the light from light pipe 24 to travel past deflector 41 to assist in illuminating the righthand or distal portions of reflector hood 42 and target site 29. Arrow 52 indicates a possible trajectory of an exemplary light ray received from light pipe 24 as it is reflected off deflector surface 50 to the dome of reflector hood 42 and thence to the surface of target site 29.

The dimensions of reflector hood 42 are somewhat larger than those of deflector 41, to provide substantial clearance for light travel past deflector 41 in all directions.

As an alternative to the optical system provided by deflector 41 and reflector hood 42, a planar or slightly convex mirror could be provided disposed at an angle of about 45° to the direction of light pipe 24 and target site 29. However, greater spreading of the light beam with more acute angles of incidence to the target site obtainable with deflector 41 and reflector hood 42, is contemplated as being desirable.

Desirably also, all the interior surfaces of neck 14 and output head 16 on which deliverable light may be incident, including the interior surfaces of reflector hood 42 and of deflector 41, have good or excellent reflectivity, being formed, for example, of highly polished aluminum. The aluminum can be vapor deposited or otherwise formed as a film on a structural material. The structural material can be any suitable moldable plastic, for example an acrylic or ABS (acrylonitrile butadiene styrene) polymer or copolymer. Alternatively, neck 14 and output head 16 can be formed of stainless steel with highly polished interior surfaces. Preferred photothermal embodiments of the invention which have a combined heat and light energy output desirably employed reflective surfacing which effectively reflects heat energy generated by light source 18 so that a desired intensity of heat energy is output from light output head 16 along with the light energy.

In another embodiment of the invention, the photothermal treatment instrument 10 is designed to intentionally attenuate heat energy generated by lamp 32 by employing reflective surfacing which preferentially reflects light energy to reduce the relative heat intensity in the energy output to a desired value compared to the light intensity.

The output beam from output head 16 is desirably controlled by deflector 41 and reflector hood 42 to be spread or divergent to a limited degree so that much of the light is incident to a plane at the surface of target site 29. This plane may represent an average surface of a suitable anatomical target having a rather irregular surface, for example, the back of the tongue or the tonsils. Desirably also, the angle of incidence of the light on target site 29 is controlled to be reasonably close to the perpendicular, for example at an angle of about 30° or even 20°, or less, to the perpendicular. Desirably, at least about fifty percent, more desirably, at least about 70 percent, of the luminous flux received on the target site 29 is incident at such an angle. Incidence at shallow angles to the target plane, for example greater than 45° to the perpendicular, is largely avoided or is reduced by appropriate design of the optical geometry. Such constraint of the output beam to be only modestly divergent or nearly parallel, is useful to enhance the penetration of shorter wavelengths, for example, blue-green wavelengths of about 400-600 nm or subdivisions of that waveband, into target tissue.

Optionally, a ring of spacers, such as brushes 54 each comprising a clump of bristles, can be provided around a periphery 56 of reflector hood 42 to space output head 16 at a desired distance from target site 29 for the application of photothermal energy to the target tissue. The bristles of brushes 54 can have any suitable stiffness, for example that comparable with a medium toothbrush or a tongue brush and may be spaced apart as shown in FIG. 3, or may be close together forming a substantially continuous ring. Brushes 54 can have any suitable length, for example, a length less than the typical 10 mm of a toothbrush, desirably less than about 8 mm, for example from about 2 mm to about 5 mm. Some brushes 54 have been omitted from FIG. 2, for clarity.

A continuous or discontinuous lip, a ring of solid pin-like projections, one or more segments of foam or sponge material or other suitable structural spacers could be employed in place of brushes 54, as will be apparent to those skilled in the art.

Brushes 54, or their equivalent, can be used to apply topical treatments to target site 29, if desired, for example a local anesthetic or an oxygen gel.

Output port 57 of reflector hood 42, which is defined by periphery 56 and which determines the size and shape of the energy pattern on the target site can have any suitable shape and size. For example output port 57 may, as shown be approximately circular, or could be oval, elliptical, triangular, rectangular or polygonal, or other suitable shape. The size of output port 57 is desirably sufficiently small for output head 16 to be accommodated in the oral or other bodily cavity without difficulty, and to be manipulated as necessary, yet large enough to avoid having to employ an excessive scanning trajectory to completely treat a desired target site 29, for example the back of the tongue or the tonsils.

Output port 57, as shown, is spaced from target surface 29 by brushes can, as stated above.

Some useful embodiments of the invention employ a photothermal treatment instrument 10 wherein the output port 57 has a large transverse dimension, or diameter or equivalent, of from about 10 mm to about 50 mm, preferably from about 25 mm to about 35 mm. If output port 57 is shaped with a smaller dimension, the smaller dimension can be at least 15 mm, for example from about 20 mm to about 30 mm. In one embodiment of the invention, output port 57 is approximately circular with a diameter of from about 30-35 mm and in another embodiment, output port 57 is oval or elliptical with a major dimension of about 30-35 mm and a minor dimension of about 25-30 mm. Clearly, light output head 16 should be no larger than can be accommodated in a bodily cavity where treatment is to be applied, and may in many embodiments, have dimensions transverse to the direction of neck 14, the distal direction, which are no greater than 50 mm, or even no greater than 40 mm.

Following these general guidelines the surface area of the pattern of useful energy on the target site can be from about 25 to about 1,500 mm$^2$, more preferably from about 100 to about 1,000 mm$^2$. Within these limits, depending upon the accessibility of the target site, the power of the light source and the desired dosage, it is desirable to have as large an energy pattern as possible, for example at least about 300 preferably at least about 500 mm$^2$, to simplify or shorten the treatment protocol. It will be appreciated that output port 57 and the other components of photothermal treatment instrument 10 can have any structure which will provide such energy pattern areas on a desired target site with sufficient energy intensity to provide effective microorganism control.

It will be understood from this description that many, but not all, embodiments of the invention may have a light output head 16 which is substantially larger than a toothbrush, having, for example, lateral dimensions transverse to the direction of neck 14 that render it unsuitable to fit alongside the teeth or in the cheek.

Arrow 59 indicates the width of the projected energy pattern on the target, within the fringes of the pattern where there is a substantial drop-off in intensity. The pattern width will usually be at least as large as output port 57, and more commonly, where the beam pattern is divergent, somewhat larger, perhaps 10-30 percent larger than output port 57. It will be understood that this percentage can be increased by increasing the spacing of output head 16 from target site 29 when energy is discharged, for example by increasing the height of brushes 54 or other spacers, or simply by holding the photothermal treatment instrument 10 at a greater distance from target site 29. However, increasing the spacing reduces the intensity and may reduce the effectiveness of a treatment or require more prolonged treatments.

In many, but not all embodiments of the invention, the energy pattern on the target, as indicated by arrow 59, is surrounded by spacer brushes 59 and not contacted by any light-transmitting component of photothermal treatment instrument 10. Also, as described above, many, but not all, embodiments output port 57 is spaced apart from target site 29 so that air or ambient gases or vapors at the target can pass between target site 29 and output port 57. If desired, output port 57 could be covered by a cover (not shown) of suitable clear, light- and heat-transmitting material. However, such a cover is contemplated as being subject to contamination which may reduce energy transmission and may also be subject to heating or to developing hot spots if contacted with target site 29 which could cause tissue damage, discomfort or pain. Accordingly, it is preferred that contact with target site 29 by such cover, if employed, be avoided.

In many, but not all, embodiments, the output energy travels entirely through air, breathe or other patient-generated gaseous mixture from filter 34 or 36, or from lamp 32 if no filter is employed, to target 29.

Another optional feature of the invention illustrated in the embodiment of FIGS. 1-3 comprises a thermosensor 58 to read the temperature of a treated target surface. Thermosensor 58, if employed, could be a separate instrument but is preferably carried on output head 16. Thermosensor 58 can be mounted on any convenient location on output head 16 where the thermosensor will be protected from direct exposure to the applied energy, and can read a temperature off the target site 29. An example of one such location is on the underside of deflector 41 where thermosensor 58 could be wired through strut 49. Alternatively, thermosensor 58 could be located between brushes 54 on the underside of output head 16 or on neck 14 adjacent output head 16. Thermosensor 58 is preferably disposed, oriented and constructed to read the temperature of the target surface treated by photothermal treatment instrument 10 and to be largely unaffected by the radiation delivered by photothermal treatment instrument 10.

As an alternative to a radiative thermosensor such as thermosensor 58, the temperature of the target tissue can be determined by contact means. For example a temperature needle probe or an electro-needle probe can be used to determine the temperature at the back of the tongue or at another target tissue surface. It will be understood that temperature determinations of tissue surfaces and bacterial or other microorganism colony counts can be employed in individual cases or in sample cases to calibrate a method and determine dosages that may be employed and for which photothermal treatment instrument 10 may be set or settable and which dosages are usable as reasonable averages for substantial populations of patients, e.g demographic populations such as children, adults, diabetic, immune-compromised, gerontologic and so on.

Temperatures to be measured are contemplated as being in the range of from body temperature, about 37° C., to about 65 or 70° C. and the thermosensor range can be selected accordingly. For example, the range of sensitivity of thermosensor 58 need be no more than from about 20° C. to about 100° C. or can even be a narrower range of from about 35° C. to about 75° C. although of course thermosensors with wider ranges can be employed, if desired.

If desired, a joint 60 can be provided to releasably connect output head 16 to neck 14. Joint 60 can be threaded, a push fit, snap fit or other suitable joint enabling the user to separate output head 16 from neck 14 or rotate it relatively thereto. In one embodiment of the invention output head 16 is rotatable through at least 180° between the position shown in FIG. 1 and an opposite position where light from output head 16 is directed upwardly away from the convex surface of neck 14. The one position, as shown in FIG. 1, can be employed for treating lower posterior oral cavity surfaces, such as the back of the tongue and the tonsils. The opposite head position can be employed for treating upper posterior oral cavity surfaces such as the back of the throat. Friction, detents or other latch-like means can be employed to lock output head 16 in each desired angular position relatively to neck 14. Alternatively, or additionally a similarly joint permitting rotation of neck 14 may be provided between neck 14 and body 12.

For application of radiant heat energy or, preferably heat and light energy, to the target site 29, lamp 32 is selected to be a thermal emitter having a heat transmissive glass, e.g. quartz glass, borosilicate glass or other suitable enclosure or bulb. To avoid undue attenuation of the heat energy before it reaches target site 29, photothermal treatment instrument 10 can be formed with a clear path from lamp 32 to target site 29 which is free of heat attenuating elements that are strong infrared absorbers, for example, infrared-blocking glass lenses or filters. For example, the light path through photothermal treatment instrument 10 from lamp 32 to target site 29 may be entirely through air, or other gas or vacuum, and through heat and light transmitting members, desirably members formed of quartz glass or an equivalent. Thus, for delivery of heat as well as light to the target 29, filters 36, 38, or other radiation transmissive elements between the energy source and the target, if employed, may be formed of a suitable glass such as an orange or red glass with good infrared transmissivity, e.g. quartz glass or a more exotic glass such as an infrared transmitting chalcogenide or chalcohalide glass, as is known to those skilled in the art.

Materials. Photothermal treatment instrument 10 can be manufactured of any suitable materials as will be apparent to those skilled in the art for example, moldable thermoplastic or thermosetting polymers and/or resins and may be of rigid construction. However, the invention also includes embodiments where neck 14 or light output head 16, or both, are flexible and, optionally, resilient. For example, neck 14 could be flexible to facilitate orientation or location of light output head 16. Another option is for reflector hood 42 to be deformable, permitting the user to change the shape of reflector hood 42 to better adapt hood 42 to the location or configuration of a target site 29.

Disposability. As described above, output head 16 and also neck 14 can be removably attachable to body 12 which houses light source 18 and associated electrical equipment. By making output head 16 and/or neck 14 of economical construction, for example plastic moldings, they can be rendered disposable. Thus a new head 16, optionally with a new neck 14, can be employed for each new patient, or each new treatment, avoiding need for sterilization of a component for reuse. However, if desired, neck 14 and optionally also output head 16 could be sterilized and reused for multiple treatments. Where photothermal treatment instrument 10 is dedicated to a single patient or consumer, sterilization may not be necessary.

Figure 4:
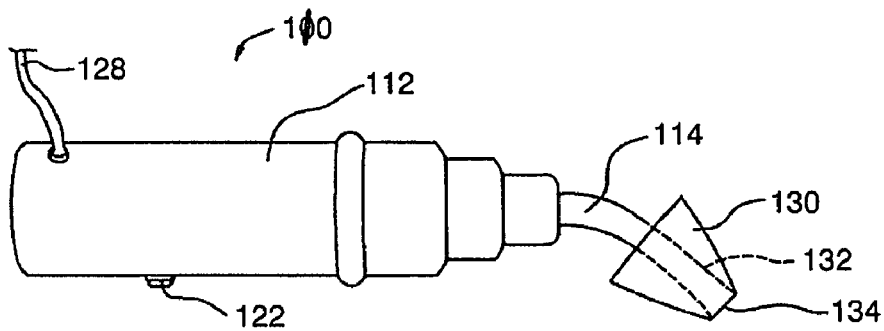
FIG. 4 is a side elevational view of a photothermal treatment instrument according to a second embodiment of the invention suitable for treating the nasal cavity.

Nasal Applicator. Referring to FIG. 4, a photothermal treatment instrument 110 for nasal applications is generally similar to photothermal treatment instrument 10 but has a modified neck and light output head to suit it to nasal treatment. Photothermal treatment instrument 110 comprises a body 112 which internally is equipped similarly to light source 18 to controllably generate and output light and externally is provided with a control switch 122 and a power cord 128 similar to control switch 22 and power cord 28 of photothermal treatment instrument 10. The external shape of body 112 can differ, as shown, from that of body 12 to be convenient for nasal application.

Photothermal treatment instrument 110 has a rather short curved neck 114 provided internally with a light pipe (not shown) similar to light pipe 24. Neck 114 extends from body 112 and is terminated by a funnel- or frustoconical-shaped nozzle 130 which is designed to be a close fit in a patient's nostril. Nozzle 130 also carries a reflectively lined light pipe 132 which can be of a constant cross-section along its length or, in one desirable embodiment of the invention, has a distally increasing cross-section to provide a flared or divergent output beam for treatment of the lower and upper nasal cavities. Desirably, nozzle 130 has a circular cross-section, although other suitable shapes may be employed, and is provided in a range of sizes to fit different nasal anatomies in a manner known generally to the art. Depending upon its size, nozzle 130 can have an outlet 134 with a diameter in the range of from about 1 to about 10 mm, desirably from about 3 to about 7 mm.

Figure 5:
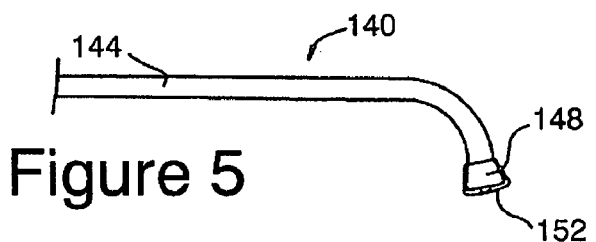
FIG. 5 is a partial view of one sinus applicator suitable for use with the photothermal treatment instrument shown in FIG. 4.
Figure 6:
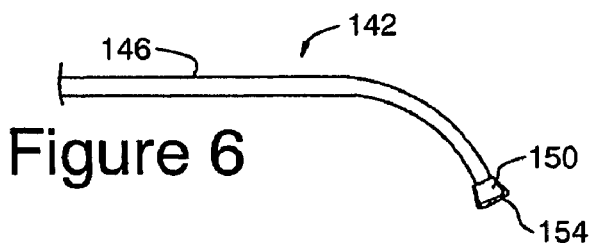
FIG. 6 is a partial view of another sinus applicator suitable for use with the photothermal treatment instrument shown in FIG. 4.

Nozzle 130 can be detachably attached to neck 114 and, desirably, neck 114 can be detachably attached to body 112 of photothermal treatment instrument 110 whereby alternative applicators such as the sinus applicators shown in FIGS. 5 and 6.

Referring now to FIGS. 5 and 6, sinus applicators 140, 142 can be provided to access a patients' sinus cavities via their nostrils and to output photothermal energy into one or more target sinus cavities. Sinus applicators 140, 142 have relatively thin elongated shafts 144, 146 respectively, to extend through the nasal cavity and terminate in relatively small nozzles 148, 150 with small outlets 152, 154 respectively, intended to direct light into a sinus cavity to be treated when the sinus applicator is suitably positioned. Sinus applicators 140, 142 are also provided with internal light pipes (not shown) which may be flared at their distal ends to provide a flared light output beam.

Alternative configurations. It will be understood that photothermal treatment instruments 10 and 110 can have a variety of alternative configurations. For example, light output head 16 could have a generally cylindrical shape, the axis of the cylinder being transverse to the longitudinal direction of neck 114 and energy being outputted generally along the axis of the cylinder. The cylindrical light output head can also be rotatable about neck 14 to facilitate orientation of the instrument to address the target. The cylinder can be open at either or both ends to output light in either axial direction, or simultaneously in the two opposed directions, according to the target surface or surfaces to be treated. For example, the back of the tongue and back of the throat or two tonsils could be treated simultaneously.

In other embodiments of the invention, neck 14 can be modified to facilitate treatment of a variety of more or less accessible sites. For example, neck 114 may comprise a flexible light pipe enabling the orientation of light output head 16 to be varied, or a telescopic light pipe enabling the effective length of neck 114 to be varied. Alternatively, neck 114 could have a flexible portion and a telescopic portion, or could even be of a flexible and telescopic construction comprising for example a pair of flexible sleeves, one fitted inside the other, and each having reflective internal surfaces. Neck 14 can also be rotatable relative to body 12 and may be provided with a gripping surface or tab or key-like projection to facilitate manual rotation of the neck. Preferably, such grippable structure is located at the base of neck 14, near body 12 to enable the practitioner to rotate head 16 while located in the patient's oral cavity.

In another alternative embodiment, electrical rather than photothermal energy is transmitted from handheld body 12 to light output head 16. For this purpose, a suitable, relatively smaller embodiment of lamp 32, e.g. a bulb-shaped embodiment, can be provided in light output head 16, in place of deflector 41, hood 42 being suitably modified. The smaller lamp 32 is supplied with electricity via conductors such as 34, extending through neck 14 from controller unit 20. Reflector 30 and light pipe 24 are accordingly not required in this alternative embodiment enabling the size of body 12 and neck 14 to be reduced, if desired.

Kits. If desired, embodiments of photothermal treatment instrument 10 can be supplied as kits comprising one or both of photothermal treatment instrument 10 and 100 and optionally one or more other similar photothermal treatment instruments adapted for treatment of other sites or for providing different treatments pursuant to the invention herein optionally together with one or more replacement light output heads 16 and/or nozzles 130 and/or sinus applicators 140 and/or 142 and optionally one or more interchangeable filters 34, 36.

Energy sources. A variety of energy sources can be employed for the photothermal treatment instruments of the invention including for example pulsed light, pulsed heat and light, and continuous or pulsed LED or laser sources. If a laser is utilized, it is preferably a low intensity or relatively low intensity laser and may optionally be provided with a diffuser to spread the output radiation. Thus a laser suitable for use in the present invention can be tuned or otherwise selected to have output characteristics specifically suited to the treatment of halitosis. Desirably the output should be such as to kill a suitable percentage, e.g. 50% of target bacteria within a relatively short time period, e.g. 0.5 to 10 minutes, preferably 1 to 5 minutes, while optionally permitting survival of a useful percentage of commensal normal microorganisms. The wavelength of the laser or other light source may also be selected to target undesired rather than normal microorganisms, e.g. gram-negative bacteria. The energy system desirably outputs energy over a target area or in a target pattern which is neither a thin pencil, which would make coverage of the target difficult, nor too wide an area which could render the received radiation too weak to be effective.

One embodiment of the invention (not illustrated) employs, as an alternative to the Azar et al. light source described hereinabove, an electromagnetic energy source such as the incoherent pulsed light sources disclosed in Eckhouse et al. U.S. Pat. No. 6,514,243, the entire disclosure of which is hereby incorporated herein by reference thereto. Eckhouse et al. employ for removal of hair from the skin by means of electromagnetic follicle destruction a gas filled flashlamp, such as a xenon-filled linear flashlamp ILC Technologies model no. L5568.

Character of Energy Output. Depending upon the nature of the organism or organisms to be controlled, the applied energy delivered from output head 16 to the target site 29 can be either heat energy alone or light energy alone but is preferably a mix of heat and light energy. The energy should be applied in a quantity and at a wavelength effective to obtain a desired reduction of the colony microorganism or microorganisms to be controlled. In one embodiment of the invention about 80 percent of the applied energy reaching target site 29 can be heat and about 20 percent can be light. These quantities can of course vary substantially and can lie in the ranges for example, of from about 60 to about 90 percent heat and about 10 to about 40 percent light.

Preferably the light energy employed includes visible wavelengths and optionally it may include a minor proportion of ultraviolet light in the wavelengths for UVA or UVB or both. However it is usually desirable to avoid UVC wavelengths which may induce DNA or other damage to human tissue. Another embodiment of the invention substantially excludes all wavelengths of ultraviolet for treatments where the potential carcinogenicity, or other potentially harmful effects of ultraviolet light are unacceptable.

While the invention is not limited by any particular theory, it is contemplated that light may often be effective to reduce superficial colonies of microorganisms at the target, i.e. microorganisms that are essentially on the surface of the target tissues. Light may also incapacitate microorganisms up to a depth of about 1 to about 1.5 mm. However, light may not adequately penetrate deeper layers of tissue harboring microorganisms, for example by being fissured or porous providing concealed volumes that may accommodate same. For example the tonsils and the tongue have deep crevices, papilla, crypts or pockets where significant populations of undesirable microorganisms may reside.

Accordingly, employment of near infrared or longer wavelength heat energy that can penetrate the superficial tissue layers and reduce microorganisms harbored in subepithelial, interstitial volumes, is contemplated as an advantageous but optional, feature of the present invention. Preferably, such heat energy is applied simultaneously with the light energy and from a common source.

By employing light energy in conjunction with mild heat energy, many microorganisms can be effectively destroyed photochemically, possibly avoiding the need to use more intense heat to raise the tissue temperature to the coagulation temperature of the microorganism. Such an embodiment of the invention can be employed where a patient has particularly sensitive, or previously damaged tissue, or there is a particular concern to avoid tissue damage. Furthermore, mild heating can increase the local blood flow, facilitating the elimination of bacteria or other microorganisms.

The applied energy can be selected to include wavelengths, in addition to visible light wavelengths, that both elevate the temperature of the target to cause thermal damage to colonies of microorganisms resident at the target and also to accelerate destructive photochemical reactions. The energy can be selected to include wavelengths absorbed by the mucous tissue at the target which is impacted by the applied radiation.

Pursuant to the invention, it is desirable to destroy microorganisms resident on or in the target tissue without damage to, or with only minimal damage to, the tissue itself and without causing the patient pain, soreness or other undesired reaction. To this end in one embodiment of the invention the tissue temperature can be raised to a temperature in the range of from about 50° C. to about 70° C., preferably to about 60° C., for example in the range of from about 57° C. to about 63° C. The temperature of the target tissue can be determined in known manner or by employing a thermosensor such as thermosensor 58 carried by the photothermal treatment instrument 10 and operated during, or preferably, promptly after application of a photothermal treatment.

If desired the instrument can be calibrated by performing a number of treatments with different durations, intensities and targets and detecting the resultant target temperatures. Using this information settings and protocols can be provided for future procedures that will yield appropriate target temperatures with reasonable confidence, without the need for real time temperature determinations.

The period of elevated temperature is preferably of the order of about 1 minute for example from about 5 seconds to 5 minutes or in the range of from about 20 seconds to 2 minutes, or from about 40 to about 80 seconds. A desired period of elevated temperature may be achieved by application of one or more energy pulses, up to no more than about ten pulses within the period, each pulse being of brief duration, as described herein, and each being followed by a quiescent interval providing for tissue relaxation.

Pulsed and continuous energy flux. Some useful embodiments of the invention employ pulsed rather than continuous energy sources to provide high peak power and efficient photochemical activation of harmful chemical species in the microorganisms or in treatment materials such as oxygen gels, if the latter are employed. Other embodiments can employ continuous energy sources, if desired.

In the application of heat, use of a pulsed source can be helpful as pulsing allows for thermal relaxation of the tissue in the troughs between peaks preventing localized overheating of, and damage to, tissue.

Useful pulsed radiation for practicing the invention can have a pulse width of not more than about 200 msec, for example from about 10 to about 100 msec. In one useful embodiment of the invention the pulse width is about 25-35 msec. If multiple pulses are applied at one time, there is desirably a delay, providing a tissue relaxation interval between pulses of the order of from about 10 to about 2000 msec, desirably from about 20 to about 100 msec, for example about 40 or 50 msec, to permit tissue relaxation and prevent tissue damage.

The pulse energy delivered to the target site should be sufficient to be effective in controlling microorganisms without causing tissue damage such as to be normally perceived by the patient or that would be harmful to the patient. For example, energy pulses of from about 0.1 to about 5 J/cm$^2$, preferably from about 0.5 to about 3.0 J/cm$^2$ may be employed. Constant energy application may be at suitable or equivalent intensities. Useful intensities may lie in the range of from about 1 to about 1,000 milliwatts/cm$^2$, e.g. from about 10 to about 200 milliwatts/cm$^2$ or from about 25 to about 100 milliwatts/cm$^2$.

If employed, the heat energy may be provided by any suitable source, for example infrared radiation, convection, conduction or in situ induction by RF or microwave energy or the like. If desired, RF or microwave energy may be applied to obtain useful therapeutic results in conjunction with light and/or a heat source. It will be understood that RF or microwave or equivalent energy fluxes can be employed to provide useful microorganism control effects by mechanisms other than local heating, for example by electroporation (cell membrane pore formation) or cell membrane rupture. Some, but not all, useful embodiments of the invention employ light, optionally in combination with another energy source.

The electromagnetic energy can be applied in any suitable wavelength mode, waveband mode or combination of wavelength and/or waveband modes which is or are effective to provide control of one or more target microorganism species without causing unacceptable pain, trauma or other side effects. A suitable source or combination of sources can be provided to generate or introduce the desired energy or energy mix in situ.

For example, any combination of two or more of light energy, heat energy, radio frequency ("RF") and microwave energy may be employed in the inventive treatments, if desired. Some useful treatment embodiments of the invention apply light energy together with heat energy and may optionally also apply RF or microwave energy. In alternative embodiments, a light energy mode is employed together with a heat energy mode, a microwave or RF mode or with a heat energy mode and a microwave or RF mode. Useful embodiments include heat energy modes wherein the heat energy is generated by RF or microwave radiation. Alternatively, the heat energy mode may comprise infrared radiation.

The invention includes embodiments wherein two or more energy modes are applied essentially simultaneously. By "essentially simultaneously" is meant that the two energy modes are applied simultaneously, or are applied in rapid succession, one after the other, such that significant cooling of the target does not occur between the first and second applications of energy.

Each energy mode source or applicator can be any suitable device as known to those skilled in the art. Combination devices and methods such as disclosed in Kreindel U.S. Pat. No. 6,702,808, the entire disclosure of which is hereby incorporated herein by this specific reference thereto, can also be employed. The invention includes novel uses of such devices and novel combinations and modifications of such devices adapting or combining them for the purposes of the invention, as will be apparent to those skilled in the art in light of the disclosure herein.

By way of example, the energy applicator device can include a light source to emit optical energy, one or more electrode pairs for generation of RF energy and/or microwave elements for generation of microwave energy. Optionally, the light source may also provide an effective intensity of heat energy. Pulsed RF energy applied by the electrodes can be applied to the target tissue either directly or through a conductive substance.

Usefully, the frequency of the RF energy can be in a range of from about 300 kHz to about 100 MHz, the output power can be from about 5 to about 200 W, pulse duration from about 1 to about 500 msec and the pulse rate can be from about 0.1 to about 10 pulse per second. Frequencies, or frequency ranges, in spectral locations assigned by governmental entities for industrial, scientific and/or medical purposes are particularly useful, including for example in the United States, FCC-assigned frequencies of about 13.56 MHz, 27.12 MHz and 40.68 MHz.

The optical energy employed with such an RF energy mode can have an intensity of from about 5 to about 100 Joules/cm2 and a pulse duration of from about 1 to 200 msec. The individual or combined energy dosages desirably are selected to avoid long-term physiological damage or unacceptable discomfort pain or other immediate adverse effects.

Visible light, if employed, may have a single wavelength, multiple wavelengths or a waveband and this or these are preferably selected according to the absorbency of the target organism or organisms, and are typically in the range of 500 to 1200 nm. Other energy modes, if employed, may also have a single wavelength, multiple wavelengths or a waveband or wavebands.

Microwave energy for use in the invention can be of any suitable frequency for example in a range of from about 100 MHz to about 50,000 MHz, the output power can be from about 0.01 to about 10 watts/ml of target volume, optionally from about 0.1 to about 2 watts/ml. Frequencies, or frequency ranges, in spectral locations assigned by governmental entities for industrial, scientific and/or medical purposes are particularly useful, including for example in the United States, FCC-assigned frequencies of about 915 MHz, 2,450 MHz, 5,800 MHz and 24,125 MHz.

Selection of a suitable energy mode or mix of energy modes to provide an effective treatment can be made on the basis of the teachings herein with the assistance of knowledge in the art, if desired. For example, useful guidance regarding antimicrobial energy treatments may be found, inter alia, in the food processing arts, for example in disclosures such as the USFDA Center for Food Safety and Applied Nutrition publication "Kinetics of Microbial Inactivation for Alternative Food Processing Technologies", dated Jun. 2, 2000, the entire disclosure of which is hereby incorporated herein by this specific reference thereto. Of particular interest is the section headed "Microwave and Radio Frequency Processing" and section 3.3 thereof.

RF and microwave energy fluxes are useful for their rapid and uniform effect and ability to penetrate subepithelially to reach microorganisms harbored in tissue crevices, folds, pockets and the like and organisms overlaid with other material, e.g. coatings or other microorganisms. Suitable guides and screens or other protective structure can be provided to introduce the desired energy flux to the target area while protecting the subject anatomy from incidental harm. The intensity and duration and other characteristics of the energy flux can be selected with these objectives in mind, without undue experimentation, and pursuant to the principles described in more detail herein for application of light or heat.

The invention includes treatment methods employing a mix of energy modes selected to provide comprehensive therapy at a target site by killing or otherwise controlling a broad spectrum of undesired microorganisms resident at the target site wherein effective energy dosages are applied so as to reach not only superficially resident microorganisms, but also deeper layers or volumes of the target site that are believed to harbor undesired microorganisms. When safely introduced to the target site, RF or microwave energy fluxes are believed useful to this end for their relatively uniform or distributed effects in solid materials especially high water solids such as tissue or other anatomical structures.

Colony count. In one embodiment of the invention, the photothermal treatment is applied in a manner such as to obtain a desired reduction of colony count of a target microorganism or microorganisms, for example a broad spectrum bacterial infection or infection by an antibiotic-resistant strain or strains of bacteria. Pursuant to this embodiment of the invention, parameters such as the intensity and spectrum of the applied energy and the duration of treatment are controlled to obtain a desired colony count reduction of the target microorganism.

The colony count reduction in a given energy dosage may for example be at least 70%, or preferably at least about 90%. A 90% reduction can generally be effected by applying twice the $LD_{50}$ for a given target organism or an average of the $LD_{50}$'s for a spectrum of target organisms. The bacterial colony count can be determined by taking a biopsy of the target site 29 using a scraper, swab or the like and cultivating the biopsied tissue through serial dilutions and determining the colony counts by known methods. Determinations of colony count reduction can be employed to calibrate the energy output of photothermal treatment instrument 10 to output one or more specific dosages determined to elicit a particular response in a patient or group or class of patients. Optionally photothermal treatment instrument 10 may have settable controls to provide different predetermined dosages, which controls may be labeled. For example, a duration controller may be provided for selecting the pulse duration or pulse width e.g. from about 10 to about 50 msec, and a pulse number selector may select the number of pulses output for a single actuation of photothermal treatment instrument 10, for example from 1-10 pulses, at a predetermined relaxation interval, for example of from about 10 to about 100 msec.

As described, the inventive treatments can be performed to obtain a desired temperature elevation of target tissue for a predetermined period of time or to obtain a desired microorganism colony count reduction. The treatments can also be performed to elevate the target tissue to a selected temperature or temperature range for a duration sufficient to obtain a desired colony count reduction in a target or sample microorganism or spectrum of microorganisms.

Chemical supplementation. If desired, various chemical means can be used to supplement the effect of the radiation or to sensitize the target microorganisms to the radiation. For example, the treatment may be a photochemotherapeutic treatment, for example by employing an oxygen gel or other suitable material containing a biocompatible oxidant, e.g. hydrogen peroxide, in a concentration of from about 0.5 to about 5% by weight of the gel. The oxidant chemically sensitizes the bacteria or other microorganisms to the effects of the applied radiation.

Alternatively, the target organisms may be stained, e.g. with a food dye, to enhance the absorption of light. If staining is employed the stain color can be selected to correspond with the applied light wavelengths, to enhance the effect, for example by using a blue or green stain with applied orange or red light and a red or orange stain with applied green or blue-green light.

Such gels, stains or other target treatment compositions, for example local anesthetics, can advantageously be applied employing the spacer elements constituted by brushes 54, if desired, or other suitable applicator as is known. For example, a local anesthetic, e.g. 4 percent XYLOCAINE (trademark), Astrazeneca LP, can be applied to the back of the tongue to suppress the gagging response, if desired, for posterior oral cavity treatments, pursuant to the invention.

Target sites. The method and instruments of the invention, employed separately or together, can be employed to treat a variety of nondental target sites 29 to control microorganisms infecting the target site. Suitable target sites 29 include internal body sites located in externally opening body cavities or body cavities that are otherwise accessible without need for a catheter, for example, in the upper respiratory tract.

Dental regions of the anatomy are subject to special considerations regarding bacterial or other infections. Unique organisms may be implicated in the diseases of the teeth and the periodontal region and the distinctive nature of pathologies such as caries and gum disease render the treatment and prognosis of dental region infections to lie largely in the province of the profession of dentistry.

Figure 7:
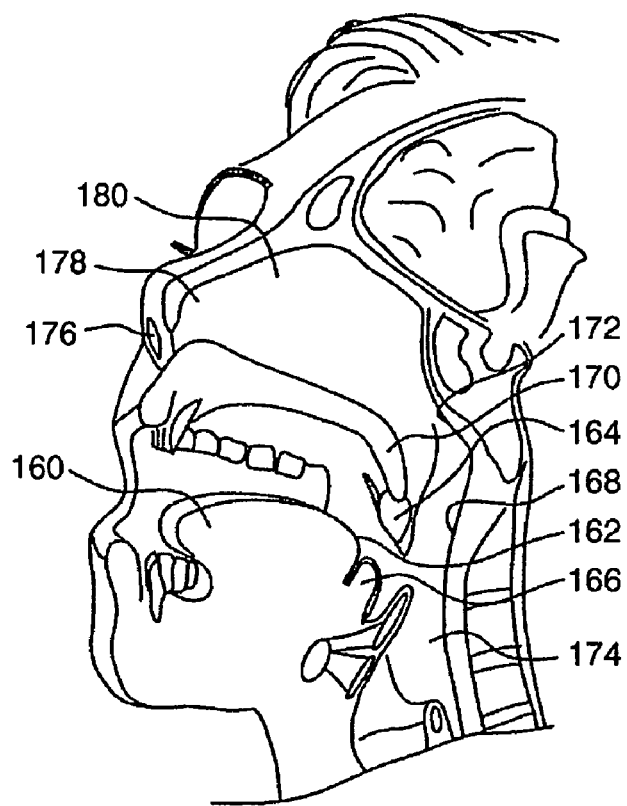
FIG. 7 is an anatomical vertical section through a human head illustrating some target treatment sites for the methods of the invention.
Figure 8:
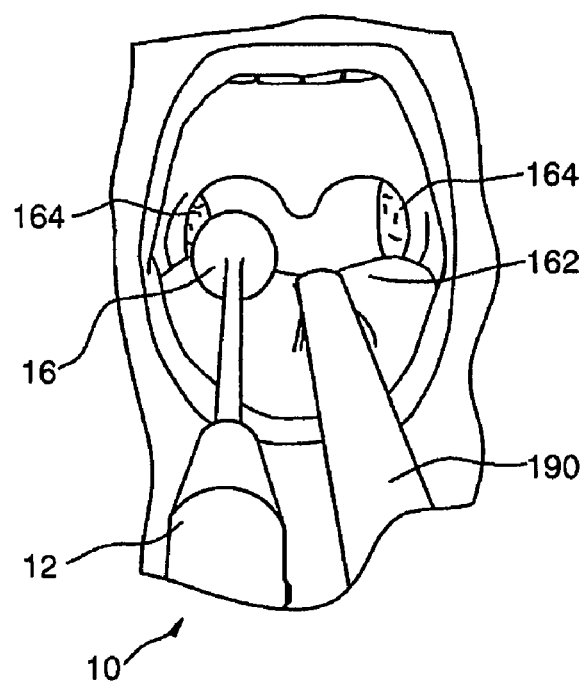
FIG. 8 is a partial view of the oral cavity of a patient during a photothermal treatment according to the invention.

Some suitable upper respiratory tract target sites 29 are illustrated in FIG. 7. Exemplary sites include, without limitation, the tongue 160, the back of the tongue 162, the tonsils comprising the palatine tonsils 164 (one shown), the lingual tonsil 166, the pharyngeal tonsils also called the adenoids, the pharynx 168, the uvula 170, the nasopharynx 172, the laryngopharynx 174, either or both nostrils 176 (one shown), the left or right lower nasal cavity 178 (one shown), the left or right upper nasal cavity 180 (one shown), the sinuses, especially those sinuses that are accessible via the nasal cavity and the frontal, ethmoidal, sphenoidal or maxillary sinuses. If desired substantially all the pharyngeal lymphoid tissue, including the palatine tonsils, lingual tonsils, adenoids, and pharyngeal wall lymphoid vegetation may be treated. This anatomical region is sometimes called "Waldeyer's Ring".

Various suitable instruments, including the instruments described herein, for treating one or more target sites, as well as other suitable target sites, will be apparent to those skilled in the art in light of the disclosure herein.

Target conditions. Target conditions that can be treated by the methods and instruments of the invention include low-level or chronic infections of microorganisms comprising bacteria, fungi, viruses and any other microorganisms that may be present at the target site. The inventive treatments are broad spectrum and are contemplated to be active or effective against each of the foregoing classes of microorganisms. In particular the photothermal treatments of the invention are contemplated to be effective against antibiotic-resistant bacteria and anerobic bacteria. Furthermore, the treatments of the invention can be controlled to be effective against nonplaque bacteria and the invention includes treatments limited to control of nonplaque bacteria and other microorganisms. An ability to effectively treat antibiotic-resistant bacteria is especially advantageous.

Some of the conditions that can be treated include halitosis or bad breath, soreness of the tonsils or throat, stuffy or runny nose, streptococcal or other bacterial or viral infections of the posterior oral cavity and/or the pharynx, viral infections such as colds of the upper respiratory tract, influenza, sinusitis, congestion and other low-level chronic infections of the upper respiratory tract. In general, bacterial, viral, fungal, or other infections by microorganisms, of accessible surfaces, especially non-dental mucosal surfaces of the upper respiratory tract, as described above, or as otherwise apparent to those skilled in the art, can be treated by the methods and devices or instruments of the invention.

Methods of Treatment. The microorganism control treatments and instruments of the invention are particularly suited for professional use, for example for use by suitably licensed medical practitioners to treat patients in their offices. However, the invention is not so limited and can be practiced in any suitable location, including hospitals and homes. Suitable treatment protocols may vary according to the severity and persistence of the infection, the responsiveness of an individual patient and the persistence of patient-perceived symptoms. Suitable treatment protocols can comprise diagnosis of a condition and its proximate cause, an individual energy application procedure as described herein, performed on one or more infected target surfaces to a desired conclusion, such as a tissue temperature elevation or microorganism colony count reduction, repeated as infrequently as biweekly or even monthly, continued indefinitely, e.g. for two or more years, or more desirably for no more than about one year. Other desirable embodiments of the invention comprise more frequent such procedures continued for shorter periods, for example from one to five times per week, desirably once or twice per week, for periods of from about two to about sixteen weeks preferably from about four to eight weeks for example for five or six weeks.

Individual procedures can comprise one or two shots of energy applied for example to the back of the tongue and to each palatine tonsil and/or other target site 29. In another embodiment, a pulsed treatment is scanned across a target area in a number of individual steps. Each individual procedure can have a duration of from about 10 seconds to about 10 minutes, preferably from about 30 seconds to about 2 minutes, per target site referring to the time that a treatment instrument is disposed to direct energy toward the target surface.

Preliminary steps of the treatment procedure can comprise verifying the patient's condition, for example as being a chronic halitosis suffered, and diagnosis of a proximal cause of the condition as being an upper respiratory tract infection, for example a bacterial infection of the back of the tongue or one or more tonsils.

To perform a desired procedure on a patient to treat one of the described target conditions employing photothermal treatment instrument 10, the medical practitioner initially determines the desired energy output of the photothermal treatment instrument 10 by selecting an appropriate lamp 32 and filter or filters 34, 36. In addition, the practitioner sets controls for power output and duration of energy output to values selected to be appropriate for the target condition, if such controls are present.

The patient is prepped as necessary for example, by employing a mouthwash or gargle or other appropriate hygiene treatment, and by application of one or more desired locally acting agents to the target site or sites, for example an oxygen gel or a local anesthetic such as is conventionally used orally or in the pharynx, for example a spray of 4 percent XYLOCAINE (trademark), Astrazeneca LP.

Usefully, such prepping or pre-treatment steps may include removal of superficial microorganisms from the target areas and optionally also from the vicinity of the target areas to facilitate access of the primary treatments, for example the xenon flashlight radiation applied in Example 1, to the target organisms which may be lodged in deeper folds, crevices or fissures of tissues such as the back of the tongue and tonsils.

Superficial cleansing to remove microorganisms with or without desquamation, may be effected chemically, by applying an effective quantity of chlorhexidine or other suitable broad spectrum antibiotic. Alternatively, the pretreatment may be effected mechanically using a suitable surgical scraping or ablation device or process, to mechanically remove superficial organisms, and possibly a layer or layers of epithelial tissue cells. For example, a simple manual scraper or brush may be employed. Alternatively a powered vibrating or oscillating scraper, brush or other suitable abrading device, optionally ultrasonic, may be employed. Carefully controlled laser ablation could be employed if desired in the pretreatment.

Both chemical and mechanical means can be employed, if desired. Gels can be used in an effective amount to retain a chemical or biochemical agent in situ for longer periods than liquid agents, if desired. Desirably, the pre-treatment can be effected without causing inflammation or pain. If desired or helpful, a local anesthetic may be applied as an initial element of the pretreatment to control pain or, if appropriate, the gagging reflex.

Desirably also the extent or degree of the pretreatment is monitored by the practitioner to determine a suitable end point, which may be indicated, for example, by the exposure of pink tissue, without reddening. Optical aids may be employed to assess tissue color if desired.

The pretreatment may be applied to any appropriate tissue or other anatomical surface to be treated or any proximate such surface, as may be determined by the medical practitioner or other user. Exemplary such surfaces include the back of the tongue the lingual, palatine or other tonsils, surfaces showing whitening or other discoloration commonly associated with the presence of abnormal microorganim populations, or surfaces from which sulfur-containing gases may emanate as determined by suitable tests.

Useful objectives of such pretreatments may be twofold: removal of undesired microfloral growths and removal of a layer or layers that may be opaque to radiation that is to be applied in the primary treatment, thereby enabling the radiation to access deeper seated organisms.

EXAMPLE 1

Treatment of Chronic Halitosis

A patient presenting with chronic halitosis is diagnosed with a bacterial infection of the tonsils and is treated, using photothermal treatment instrument 10 as shown in FIGS. 1-3, equipped with a xenon flashlight and a blue filter, transmission about 400-500 nm, with two photothermal energy pulses of about 35 msec, with a 50 msec interval, at an energy density of about 2.5 J/cm$^2$. Two shots are applied to each palatine tonsil and two shots are delivered to the back of the tongue. In each case, light output head 16 is advanced into position with brushes 54 closely adjacent to or touching the target tissue. The procedure is repeated twice a week for six weeks. At the end of the treatment period little, if any halitosis can be detected.

FIG. 15 shows an embodiment of a treatment system according to the invention complete with a power supply, in use treating a patient. The system includes a power supply 320 shown as a "black box" which is suitable for powering the described pulsed xenon arc flashlamp embodiments of the invention, such power supplies being per se known to those skilled in the art. Power supply 320 can comprise a pulse-forming network, employing high voltage capacitors and inductors, or other suitable circuitry, and a connection for a utility power supply. If desired, a battery, preferably rechargeable, may be included for standby or portable use. The output pulse has characteristics suitable for energizing flashlamp 200 or 300 including suitable pulse energy and duration and high voltage peaks. Suitable peak voltages can be as known to those skilled in the art and may be in the range of about 1 to about 20 KV, being for example from about 5 to about 10 KV. Depending upon the particular light-emitting device employed, other suitable voltages may be used.

An insulated flexible power cord 322 can carry the power output from power supply 320 to a handpiece such as handpiece 324, which is here shown as an integral one-piece unit from which power cord 322 may be detached, if desired. Alternatively handpiece 324 can be permanently secured, e.g., by molding, to power cord 322.

Handpiece 324 includes a suitable, manually grippable portion 326 and a flashlamp head 328 containing or supporting a flashlamp, which may be substantially as described with reference to FIGS. 9-13, subject to variation as described herein, or as will be apparent to those skilled in the art. A conveniently operable switch such as a pressure pad or button 330 is provided to enable the practitioner to activate the instrument as desired. Switch 330 can take many forms, for example mechanical pushbutton, pressure pad, heat sensor and the like, as may be desired.

Conductors 331 carry the high voltage from power unit 320 to flashlamp 300, as described above. Handpiece 324 can have an exterior form that is curved and smoothly contoured to be ergonometric and easily and comfortably manipulated by the practitioner. A slim fingerlike configuration enables handpiece 324 to be inserted into the mouth and properly located to treat the back of the tongue.

Power unit 320 can have user-settable controls to provide a desired photothermal output enabling the operator to choose from a number of available selections of pulse energy, pulse duration, number of pulses and so on. The number of selections can be for example from 2 to about 10 or may be continuously variable. Preferably, an electronic display is provided to give a visual indication of the settings. Also, power unit 320 may provide a number of treatment selections each representing a particular combination of pre-set output characteristics suitable for a particular purpose, for example, for treating a specific bacterial strain, a specific patient condition a particular halimeter reading or other suitable parameters. The programming of same can be managed by a microprocessor and suitable software if desired.

Such a system can give the practitioner a "one-touch" dosage, which could include several energy pulses of selected character, for a particular diagnosed patient condition or parameter to be treated. Such a computerized power unit or other suitable control unit, could be end-user programmable employing removable compact flash cards or other suitable data storage volume or the like. It will be understood that such a computerized power unit may be employed with any of the embodiments of the invention described herein and could be built in or integral with the handpiece or could be pluggably connectable therewith to provide an integral unit.

In use, prior to a treatment, the practitioner can, if appropriate, select a suitable data storage volume containing desired treatment configuration data, load same to the computerized power unit, and make one or more program selections to configure the treatment device to generate an energy dosage having parameters appropriate for the patient to be treated, in response to one or more manual actuations of an actuator such as a button.

As an alternative to the use of an incoherent light source such as the pulsed photothermal flashlamp described hereinabove, a laser light source may be employed. In one embodiment the laser source is tuned to a peak bacterial absorption wavelength which may correspond with the natural or artificially stained or otherwise induced color of the target bacteria. Preferably, a specific applied wavelength, or waveband is selected for each organism or group or class of organisms to be treated. Thus, the source can be attuned to the target.

Colorless bacteria may be colored to enhance absorption of lethal energy doses by staining the target area, and bacteria resident in the target area, with a suitable stain, for example a blue or a pink stain. The laser wavelength can then be selected to be in the waveband complementary to the color of the stain, for example blue-green for a pink stain or yellow-orange for a blue stain, light energy having a complementary hue being strongly absorbed.

Black bacteria, for example *Prevotella intermedia*, absorb any wavelength and can be targeted with a particularly effective or practical wavelength, or wavelength peak, e.g., red, orange or $CO_2$.

Laser energy can be brought to the treatment site by any suitable means for example optical fibers. Alternatively, a laser source, e.g. one or more laser diodes, can be distally mounted in, on or near the treatment head, for example in place of the distally mounted flashlamp 200 or 300 described with reference to FIGS. 9-14. A laser source can be employed for spot treatments or for treatment of precisely defined targets employing pulses of duration selected to obtain the desired bactericidal result without tissue damage. In another embodiment, a cylindrical diffuser is provided to spread the laser light.

A further embodiment of the invention enhances the staining process by covalently coupling a suitable stain to an antibody to the target microorganism which acts as a vector or carrier directing the stain molecule to the target microorganism. Coupling can be effected by known methods, for example diazotization. Small dosages of antibody-coupled stain can enable great efficiency, ensuring that the stain reaches and is attached to target bacteria or other target microorganisms and can permit a reduced dosing of the patient's tissue with stain which is a visually and in other ways undesirable material. Such antibody coupling can be particularly beneficial when employed with a photodynamic stain, as described hereinbelow.

An advantage of staining or otherwise sensitizing the bacteria or other target organism is that the organism may become sufficiently sensitive to applied photothermal energy that quite brief energy pulses are effective to weaken, disable or destroy the bacteria. Suitable pulse durations may be as short as a few hundred picoseconds or from about 0.5 to 100 microseconds, e.g. about 1 microsecond or other duration in the range of about 1 to about 10 microseconds. The brevity of such energy pulses enables relatively high energy densities to be employed with low risk of damage to the ambient tissue. For example, when treating the back of the tongue, halitosis bacteria may be heated to a lethal level with little if any heating of the surrounding tissue.

Useful energy densities for such pulsed treatments of stained halitosis bacteria can be in the range of from about 0.5 to about 50 joules/cm$^2$, referring to the value of the energy density at or near the target tissue. Some embodiments of the invention can employ energy densities of from about 3 to about 20 joules/cm$^2$, for example from about 7 to about 12 joules/cm$^2$. The peak energy waveband can be selected to be at, to include, or to overlap the bacterial stain sensitization peaks, for good efficiency.

Another way to efficiently target halitosis or other bacteria or microorganisms to be treated and control risks of tissue damage or other adverse reactions is to sensitize the target bacteria, or ambient tissue harboring same, with a photodynamic bacterial toxin. One example of a suitable such toxin is methylene blue which, at low concentrations may be per se harmless to tissue and bacteria and which can be activated, for example by application of photothermal energy as described herein, to liberate a toxin which kills or weaken bacteria stained or otherwise exposed to the photodynamic toxin. The bactericidal effectiveness of methylene blue or other such photoactive chemical agents against anaerobic bacteria can be enhanced by also applying oxygen. Employment of photosensitizing agents, for example stains such as methylene blue, to color otherwise colorless microorganisms can enhance the absorption of destructive visual energy wavelengths. The lethality of the energy application may thus be enhanced, whether or not the stain liberates toxic agents, as is described in more detail below.

To this end, in another aspect the invention provides a novel tissue treatment system wherein both fluid and optical delivery systems are mounted in a single combination handpiece. The combination handpiece can comprise the addition of a, or a side-by-side pair of thin spray tubes each of which is optionally equipped with a suitable nozzle, to any of the treatment devices described herein, enabling a small liquid spray to be applied to the target surface. Desirably, the spray tubes are aligned with the optical head so that fluid and electromagnetic energy are directed to the same target site. The spray tubes can have an adjustable orientation relative to the optical head and may have adjustable or interchangeable nozzles to provide a selection of spray patterns. A rinsing tube can also be provided, if desired.

Photodynamic toxins such as methylene blue or a variety of other treatment fluids can be dispensed, as will be apparent to those skilled in the art, for example, bacterial stains, local anesthetic gels, or lower viscosity, sprayable equivalents thereof, and any other fluids described herein.

The optical delivery system is preferably configured to operate at wavelengths suitable for activating photodynamic compounds and may for example comprise a ~760 nm diode or a lamp filtered to a waveband which activates methylene blue or at another wavelength suitable for a different photodynamic toxin which can be activated in situ with photic or thermal or photothermal energy.

In another embodiment of the invention, the combination applicator may optionally include an oxygen supply tube to provide oxygen to the target site to enhance the in situ activation of methylene blue, and optionally in addition, a rinsing tube.

In a further embodiment of the invention, the combination applicator may include an oxygen supply tube to enhance the in situ activation of the photodynamic toxin.

Methylene blue is a photodynamic stain which is not harmful to tissue and which may be employed in the invention. Methylene blue converts into a toxic compound when irradiated with light at specific wavelengths for example a 630-700 nm light source or a UVA 340-380 nm source. Methylene blue activates tissue and ambient oxygen and converts it into a free radical which poisons both bacteria and tissue. By attaching the stain to an antibody which is specific to and can attach to a Halitosis bacteria, staining can be rendered selective. Thus, the poisonous action of the irradiated stain can destroy bacteria while leaving the tongue or other tissue substantially unaffected or unharmed.

Methylene blue can be applied, in conjunction with photothermal bactericidal therapy, employing devices or instrumentation such as described hereinbelow or will be apparent to those skilled in the art in light of this disclosure.

The invention also includes methods and apparatus that enable the dosage or dosage protocol to be selected or adjusted according to the severity of the patient's halitosis condition. An initial step comprises detecting and quantifying the patient's oral odor for which various methods are known. The determination may be made organoleptically employing a subjective odor rating assessed by a physician or other third party smelling the breath. The determination can also be made by employing analytical techniques based upon gas chromatography, mass spectrometry, cryo-osmoscopy, or the like. Data obtained from these methods can be used to enable the practitioner to select an appropriate dosage or protocol, or may be input to a computerized control unit which determines the dosage and/or protocol according to a predetermined algorithm.

Another embodiment of the invention employs a portable sulfide monitor, for example a HALIMETER (trademark) monitor supplied by Interscan, Chatsworth, Calif. The HALIMETER (trademark) monitor can quantify the levels of VSCs in oral breath to provide a determination of the intensity of the halitosis condition. Data obtained from HALIMETER (trademark) monitor determinations can be used as described in the immediately preceding paragraph. A further embodiment of the invention comprises the use of a sulfide monitor, for example the HALIMETER (trademark) monitor, as a sensor to determine the severity of a patient's halitosis, the output of the sulfide monitor being coupled with a control system for a light-based halitosis treatment applicator, such as the inventive devices and apparatus described herein or other applicators known or becoming known to those skilled in the art, and being used to provide a displayed of otherwise presented indication of the severity to the practitioner or as a control parameter to automatically determine one or more treatment settings such as the applied energy intensity, duration or number of repetitions.

The invention also includes processes of treating halitosis which target one or more particular bacterial species identified as causative agents of the condition. Thus, the treatment parameters can be selected to be relatively more effective against the particular one or more species, while possibly being less effective against other species. The one or more species can be selected from the bacterial species set forth herein, notably in the background of the invention section of this specification, or from other relevant species as may be known or become known to those skilled in the art.

In a still further embodiment, the invention provides methods and apparatus wherein the bacterial populations at the target are quantitatively monitored by species or strain on a relative or absolute basis. The treatment protocol or dosage can then be varied according to the data obtained regarding the increase or decrease of one or more bacterial populations with time. Thus, for example, treatment may be continued until a desired low level of one or more halitosis-causing bacteria is reached or until a desired increase in level of a bacterium associated with health is reached. Such a latter bacterium is desirably one which is present in only low levels when halitosis is manifest and at higher levels in healthy, non-halitosis suffering individuals, for example *Streptococcus salivarius*. The particular species will be known to those skilled in the art, for example as described hereinabove, or may become known.

Photosensitizing Agents

As described above, photosensitizing agents such as stains may be employed to enhance the treatment process. Desirable aspects of the invention employ a combination of stain and energy dosage which is effective, of convenient duration and aesthetic. Biocompatible photosensitizing stains showing strong absorbance of one or more peak wavelengths output by the light source or other source of electromagnetic radiation are particularly useful in enhancing the efficacy of the energy treatments or in rendering lethal energy dosages that might otherwise be innocuous. However, excess and displaced stain may be problematic and unaesthetic if the stain exhibits itself to the subject after treatment, for example, after blowing their nose.

To control such problems while benefiting from the lethality and efficacy that use of a suitable stain can bring, the stain can be employed in relatively low concentrations, for example a concentration of less than 1%, referring to methylene blue. In practice, concentrations of less than 0.1%, for example 0.08% or lower, are desirable to avoid aesthetic problems over an extended time period. In general, again referring to methylene blue, some useful microorganism lethality can be obtained with concentrations of 0.01% or greater, although extended energy exposures may be necessary at such concentrations. Some particularly useful embodiments of the invention employ concentrations of methylene blue in the range of from about 0.02 to about 0.08%. Concentrations of methylene blue in the range of from about 0.03 to about 0.06% are also believed to be particularly effective. It will be appreciated that other stains may employ different concentrations according to their efficacy as known or as determined by routine experimentation.

The invention provides an embodiment of low dosage treatment method and composition wherein a photosensitizer is employed in micromolar concentrations, in combination with non-ionizing photic radiation including at least one intensity peak in the orange-red wavelength range of from about 500 to about 700 nm. Pursuant to the invention it has been discovered that dosages of both photosensitizer and photic radiation when used in combination may be sufficiently mild to avoid damaging healthy tissue or causing pain or discomfort while the combination is effective to combat target microorganisms. For example molar concentrations of less than about 100 micromole ("µM") can be effectively employed as broad spectrum antimicrobial treatments of target surfaces, as described herein, and as selective treatments not only against Gram-positive bacteria, but also against Gram-negative bacteria. One useful range of dye photosensitizer concentration that may be employed is from about 1 to about 50 µM. Another is from about 1 to about 20 µM. Concentrations of less than about 1 µM, down to about 0.1 µM may be effective under some conditions. In one embodiment, the invention employs a low or the minimal effective dosage of stain which is sufficient to obtain a useful or desired reduction of harmful microbes. Optionally, the dosage may be selected to leave a residual population, perhaps 10 or 20% to promote the proliferation of healthy microflora.

Such modest stain concentrations may be relatively aesthetic, providing only moderate, or short-lasting coloration, yet have little, if any lethal effect when used alone. However they can provide a surprising enhancement of the efficacy of the energy treatment, reducing the effective dosage and thence the risks of physiological damage or the treatment duration.

Some photosensitizers of particular use in the practice of the invention are dyes or stains which are phototoxic to the target microorganism or microorganisms. Some specific photosensitizers which may be used in practicing the invention, in addition to methylene blue include dimethyl methylene blue, other dyes and photosensitizing compounds such for example as: photosensitizers selected from the group consisting of new methylene blue, arianor steel blue, toluidine blue, tryptan blue, crystal violet, azure blue cert, azure B chloride, azure 2, azure A chloride, azure B tetrafluoroborate, thionin, azure A eosinate, azure B eosinate, azure mix sicc., azure II eosinate, haematoporphyrin HCl, haematoporphyrin ester, aluminum disulfonated phthalocyanine, pyronin Y, neutral red and chlorines. Other photosensitizing agents may also be used, as will be apparent to those skilled in the art, for example, suitable biocompatible oxidizing agents such as dilute hydrogen peroxide and other stains such as phenothiaziniums, porphryins and phthalocyanins One useful criterion for selecting photosensitizers for use in the practice of the invention is that of having a relatively low minimum lethal dosage concentration for organisms exposed to suitable light, notably, light having a peak intensity at wavelengths overlapping with a photosensitizer absorption peak. Another useful criterion is the dark-to-light ratio of minimum lethal dosage concentration which expresses the photoactivation properties of the photosensitizer, being the ratio of the minimum concentration required to provide a dosage lethal to a given organism in darkness to the lethal concentration when illuminated. Some dyes or stains that require a fairly high minimum in darkness, may nevertheless be relatively innocuous to the target anatomy and/or commensal organisms that are natural residents of the target site when healthy. If they display a significantly enhanced activity when suitably illuminated, they may be useful in the practice of the invention. Such usefulness may be suggested by a dark-to-light ratio of minimum lethal dosage of at least 2, desirably at least 3, and more desirably 4 or more. Some useful photosensitizers may exhibit still higher ratios of 7 or 8 or more.

Some photosensitizers are less effective against gram-negative bacteria which have a protective outer membrane containing an additional membrane layer which may hinder the uptake of photosensitizing molecules. Accordingly, the invention includes embodiments employing one or more photosensitizers to treat target sites infected with gram negative bacteria, to control the gram negative bacterial population, which sensitizers are selected from the group consisting of methylene blue, dimethyl methylene blue, new methylene blue, toluidine blue, pyronin Y, neutral red and other dyes or stains known or discovered to be effective photosensitizers for gram negative bacteria.

Desirably, photosensitizers such as the haematoporphyrins which are not well taken up by Gram negative organisms, if selected for use, are employed in treating microorganism colonies that are rich in Gram positive bacteria. Various dyes such, for example, as aluminum disulfated phthalocyanine, toluidine blue, azure B chloride or methylene blue can, without limitation, be employed for treating Gram negative organisms. In embodiments of the invention practiced utilizing an He Ne laser desirably, tryptan blue or crystal violet are not employed.

Some useful combinations of photosensitizer agent and light wavelength include toluidine blue irradiated with optical or photothermal energy including a peak or peaks at or near a wavelength of about 630 nm and aluminum disulfonated phthalocyanine irradiated with optical or photothermal energy including a peak or peaks at or near a wavelength of about 660 nm.

The potential efficacy of different treatments and treatment means may be determined in simple tests, for example as described in the following Example 2:

EXAMPLE 2

Determination of Lethal Sensitization of Oral Pathogens

Suitable stain dosages for providing lethal sensitization of oral pathogens are determined in vitro by the following procedure. An objective is to determine the minimum duration of light exposure and minimum agent dilution required to achieve at least a 50% reduction in bacteria counts. Experimental tests are performed on two common pathogens using a continuously working, high intensity, red filtered halogen lamp. Red light from the filtered halogen lamp is transmitted through a flexible light guide to radiate downwardly onto petri dishes containing samples of live bacteria of species *Porphyromonas Gingivalis* and *Prevotella Intermedia* using the protocols described below.

Bacteria. *Prevoltella Intermedia* is isolated from patient sample material, identified in the laboratory using standard diagnostic test systems (Remel Inc., Lenexa, Kans., USA) and is maintained by twice-weekly subculture in thioglycollate medium (Becton Dickinson and Co, Sparks, Md., USA). *P. gingivalis* ATCC 33277 obtained from Remel Inc., is maintained by a twice-weekly subculture on CDC anaerobe blood agar (Becton Dickinson and Co, USA) and in thioglycollate medium (Becton Dickinson and Co, USA).

Light Source. The source for light energy is a continuously working, high intensity halogen lamp having a built-in 250-Watt quartz halogen light source, model I-250 supplied by Medithon, New York, N.Y., USA. Such lights are customarily employed for ear, nose or throat procedures. The light is transmitted through a flexible light guide and filtered to maintain maximum energy output at wavelengths in the vicinity of about 650 nm using a broadband red filter (Edmund Optics Inc., Barrington, N.J., USA). The light output power density measured at 3 cm distance from the end of the light guide with filter is about 50 milliwatts/cm2.

Photosensitizer. 1% methylene blue solution (Faulding Pharmaceutical Co, Paramus, N.J., USA) is used as a photosensitizer. Serial dilutions with water of initial solution with respective concentrations of 0.1%, 0.075%, 0.05%, 0.025% and 0.01% are prepared from the initial solution using sterile 10-ml bottles of normal saline and sterile syringes.

Lethal photosensitization of *P. Intermedia*. Petri dishes containing CDC anaerobe blood agar (Becton Dickinson and Co, USA) are inoculated with 0.5 ml of broth containing $5 \times 10^5$ CFU/ml and left closed at room temperature for about 10 minutes to let the broth penetrate the agar media. The inoculated plates are then exposed to 1 ml of methylene blue solution at concentrations 0.1%, 0.075%, 0.05%, 0.025% and 0.01% respectively for at least 60 seconds and then exposed to the red filtered light source for time intervals of 1 min, 5 min, 10 min and 20 min respectively. Only plates with concentrations of 0.01%, and 0.025% are used in the experiment with 20 min light exposure. Four plates are used for each experiment. Four inoculated plates that are not exposed to methylene blue or to the light source are used as controls. The controls are covered to protect them from ambient light. In order to examine the ability of light to cause killing of bacteria, inoculated plates are exposed to the red-filtered light at the same time intervals, without previous exposure to methylene blue, in the same groups of four plates. To study the ability of methylene blue alone to induce bacterial death, groups of four inoculated plates are exposed to the methylene blue solution at specified concentrations without subsequent exposure to the red-filtered high intensity light. A total of 108 subcultures is used for the experiment. Plates are incubated in anaerobic conditions in the jars using anaerobic pack kits (BBL GasPak Plus, Becton Dickinson and Co, Sparks, Md., USA) at 37° C. for 24 hours. Samples of the resulting culture growth are taken from each plate with sterile 1:L standard loop, dispensed in 1 ml of sterile NS and placed at the same media. Cultures are incubated at anaerobic conditions at 37° C. for another 24 hours, and after that the resulting colony count is performed on each plate.

Lethal photosensitization of *P. Gingivalis*. Serial dilutions of the *P. gingivalis* culture are prepared from the initial culture preserved on plates using 1:L sterile standard loop (Becton Dickinson and Co, USA) and sterile NS. A Vitek calorimeter (Hach Company, Loveland, Colo., USA) is used to achieve a final concentration of about $5\times10^3$ CFU/ml from an initial 0.5 standard McFarland suspension of $10^8$ CFU/ml. Plates containing CDC anaerobic blood agar (Becton Dickinson and Co, USA) are inoculated with the resulting suspension using sterile 10:L standard loops (Becton Dickinson and Co, USA). The plates are then exposed to the methylene blue solution at different concentrations and thereafter to the red-filtered high-intensity light source at different time intervals using the algorithm described for P. Intermedia. Plates are also incubated at 37° C. in the tightly closed jars supplied with anaerobic pack kits (BBL GasPak Plus, Becton Dickinson and Co, USA) for 24 hours, and the resulting colony count is performed on each plate.

Typical results obtainable from experiments such as those described in Example 2 are shown in Table 1 below, which describes the data as the means of four values, two each from each species, along with their standard deviations. The results for the two species were broadly comparable. Statistical analyses can be carried out using single-factor analysis of variance.

TABLE 1

Survival of Bacteria Exposed to Blue Stain and Red light
Percent of living bacteria

| Methylene blue % | Exposure to Red Light | | | | |
|---|---|---|---|---|---|
| | 0 | 1 min | 5 min | 10 min | 20 min |
| 0 | N/A | 70 +/− 6 | 75 +/− 7 | 73 +/− 8 | N/A |
| 0.01% | 70 +/− 11 | 73 +/− 6 | 69 +/− 7 | 55 +/− 6 | 51 +/− 4 |
| 0.025% | 75 +/− 14 | 67 +/− 4 | 47 +/− 6 | 48 +/− 8 | 49 +/− 5 |
| 0.05% | 68 +/− 12 | 53 +/− 10 | 32 +/− 7 | 32 +/− 9 | N/A |
| 0.075% | 51 +/− 10 | 45 +/− 5 | 26 +/− 5 | 25 +/− 5 | N/A |
| 0.1% | 35 +/− 9 | 39 +/− 12 | 28 +/− 9 | 24 +/− 4 | N/A |

Column 1 of Table 1 reports the concentration of stain employed in each culture as a percent of methylene blue, "methylene blue %". The remaining column headings describe the duration of red light exposure in each test.

Results. It may be seen from the data in Table 1 that a statistically significant reduction in bacterial colony count, with a survival rate of 50% or less can be achieved at concentrations of methylene blue of 0.05% and higher when the red light exposure is 10 or 20 minutes. No statistically significant difference is noted between the exposure for 10 and 20 minutes in either species or with any concentration of methylene blue. Exposure of both cultures to red-filtered high-intensity light source may produce statistically significant increased killing with duration as read at the time intervals of 1 min, 5 min and 10 min, with methylene blue concentration of 0.05%, and at the time intervals of 5 and 10 min with methylene blue concentration of 0.025%. Methylene blue concentrations of 0.075% and 0.1% show significant bactericidal effect even without light exposure. Some statistically significant bacterial killing can also be at a 0.01% concentration without light exposure in the P.gingivalis culture. With light exposure for 1 min both 0.075% and 0.1% concentrations of methylene blue produced statistically significant bacterial count reduction in both cultures. Little, if any statistically significant reduction in bacterial counts is noted with the exposure of either culture to the red-filtered high-intensity light source without the exposure to methylene blue.

Conclusion. The results of the study show that red-filtered high-intensity light, used in combination with methylene blue solution at a concentration of 0.01% or higher, can produce a bactericidal effect on both species examined, when a time of exposure less than 10 minutes and an accumulated energy level of 30 J/cm² are employed. Significant reduction in bacteria counts can also be achieved with combination of light exposure for 5 min and methylene blue concentration of 0.025% and light exposure for 1 min and methylene blue concentration of 0.05% and higher. Methylene blue can produce bactericidal effect on P.gingivalis at concentration of 0.1%. Exposure to red light with wavelength of 650 nm alone does not appear to produce significant killing of P.intermedia or P.gingivalis.

Furthermore, as may be seen from the data in Table 1 that a desired level of lethal photosensitization, namely killing of 50% or more of the bacteria population, of the studied oral pathogens can be achieved under the following conditions:
1. Illumination with red halogen light for 5 minutes or more using 0.05% methylene blue stain; or
2. Exposure to red halogen light for 20 minutes in the presence of a concentration of 0.025% or 0.01% methylene blue stain.

It may be understood that some useful conditions to avoid tissue damage and destruction of commensal organisms, while obtaining useful kill rates of target bacteria are, for example, 8-12 min at 0.01%, 4-6 min at 0.025% and equivalent combinations of concentration and exposure.

The useful conditions that are apparent from Table 1 and the accompanying discussion can be understood to be exemplary of a range of possible effective conditions that may be apparent, or may be determined with modest experimentation, and which may vary according to the particular stain employed, the prevalent species of microorganism and the wavelength and energy density of the applied light. For example, it is contemplated that use of a pulsed xenon photothermal light source as described herein can significantly reduce the exposure periods required for desired lethality.

Neither exposure to the halogen light for 20 minutes in the absence of a photosensitizer, in this case methylene blue, nor concentrations of methylene blue of 0.001% or 0.025%, without halogen light, appeared to be effective in killing bacteria Reduction of bacteria treated with 0.05% methylene blue alone, without exposure to light, is found to be insignificant. However, concentrations of 0.075% and 0.1% methylene blue are found to be significantly bactericidal, for the test species, even in the absence of red halogen light.

The data shows that lethal photosensitization of two common oral pathogens can be obtained employing high intensity red-filtered halogen light in the presence of dilute methylene blue verifying the value of chemical photosensitization and suitable applied light as a treatment alternative to chemical antibiotics which may induce resistance. Though not demonstrated by the tests described here, unlike chemical antibiotics, combinations of halogen light and suitable stains may also destroy non-bacterial organisms such as fungi and viruses.

Candied Photoapplicator. Referring now to FIGS. 20-22, illuminator bar 400, as shown in FIG. 20, is intended to be assembled with hollow candy 402 shown in FIG. 21 to provide the candied photoapplicator 404 shown in FIG. 22. Candied photoapplicator 404 is designed to deliver light for the treatment of microorganisms to target non-dental and dental areas in the oral cavity while hollow candy 402 is accommodated in the mouth, and is sucked by the subject or patient. The sucking yields pleasant sensations and may also deliver therapeutic agents or adjuncts contained in the hollow candy body, which therapeutic agents or adjuncts are optional elements that may be provided pursuant to the invention. Candied photoapplicator 404 is preferably designed to be resistant to ingestion of the whole device or any of its parts, to resist biting by the subject, and to resist fragmentation into pieces that can be swallowed or might constitute a choking hazard. To these ends hollow candy 402 can be selected to be constituted of a sufficiently hard candy or to have a combination of hardness and tensile strength, or toughness, that will resist biting and/or fragmentation.

To avoid choking hazards, illuminator bar 400 can be made to be too large to be swallowed by the intended subject while hollow candy 402 is sized and shaped to be comfortably accommodated in the subject's mouth. Preferably illuminator bar 400 can project externally of the oral cavity during use and can be readily gripped and manipulated.

Candied photoapplicator device 404 provides an appealing means, especially to children, of treating a variety of oral conditions as described herein, and as will be, or will become, apparent to those skilled in the art.

Illuminator bar 400 comprises a bar body 406, light switch 407 and a light head 408 mounted on and supported at one end, the distal end, of bar body 406. Bar body 406 can be fabricated from a suitable, durable rigid or elastomeric plastics or other material having good mechanical properties, for example a polycarbonate, polyacrylate, poly vinyl alcohol or other suitable polymer. Light head 408 comprises a light source 410 supplied with an operating voltage by conductors 412 embedded in bar body 406, which conductors 412 may be individually sheathed with insulation, (not shown), if desired or may be insulated by the material of bar body 406. Conductors 412 traverse the length of bar body 406 and emerge at its proximal end whence they may lead to, or be provided with terminations for connection to, a suitable power supply, for example, a removably integral power pack 413, as shown in FIG. 23.

Light source 410 may be a near-infrared light emitting diode "LED" 410 or other suitable emissive, incandescent or fluorescent light source. One suitable light source 410 comprises a 1 watt 810 nm light emitting diode such as is supplied by Agilent (USA). Another light source 410 may comprise a combination of multiple light emitting diodes, e.g. 2, 3 or perhaps 4, operating at different wavelengths, for example infrared, red, and blue, or any two of those wavelengths. The use of multiple light sources of different wavelengths provides multiple treatment modes enabling selective treatment of different types microorganisms sensitive to different wavelengths. The wavelength-differentiated light sources may be operated selectively, or simultaneously. They may be pulsed or cycled, and if desired, photoapplicator device 404, or an external power and/or control unit can include suitable control means enabling an operator to select a desired pattern of illumination. LEDs provide a compact, low cost, low power, readily controllable light source suitable for the purposes of the invention. However, other suitable light sources will be or become apparent to those skilled in the art, in light of the disclosure herein.

One suitable blue diode is an InGaN bright lamp such as is supplied by Luxeron (USA). The LED sources are small enough to be incorporated inside hollow treatment candy 402, attain a power level of 1 watt and are operable by a small power supply. In one embodiment of the invention the light emitting diode may be repeatedly turned "on" and "off" to control the heat output from the lamp in the oral cavity. Optionally, the respective durations of the "on" and "off" phases may be settable by the user or the manufacturer.

If desired, light source 410 can be a collimated source, for example a suitable laser, optionally equipped with a diffuser. However, some useful embodiments of the invention employ a non-collimated or divergent light source to provide good coverage of extended target areas, for example an LED or filament lamp.

Light head 408 further comprises a protective transparent layer 414 surrounding light source 410 and optionally defining a hollow volume 416 which can be evacuated, if desired, to provide heat insulation and to avoid transmission of shocks or stresses to light source 410. Transparent layer 414 can be formed of glass or other suitable transparent and durable material that can be safely inserted into the mouth. Transparent layer 414 serves as a barrier between light source 408 and the oral environment, protecting light source 408 from mechanical damage, e.g. from the teeth, and from chemical or biochemical damage such as corrosion by or current leakage to the saliva or the subject's anatomy. Transparent barrier layer 414 also protects the subject from adverse effects of possible mechanical damage to, or corrosion of, light source 408 which might occur without barrier layer 414 or an equivalent thereof. A male connector 418 is carried by or integrated into the distal end of bar body 406 to receive hollow candy 402. Male connector 418 can, by way of example, be screw threaded or provided with another type of suitable releasable fitting, for example a bayonet fitting. If desired, a switch (not shown) can be provided conveniently located on bar body 406, for example toward the proximal end thereof, to control the operation of light source 408, which switch may optionally include a timer to turn light 408 off after a preset time interval, for example 1, 2, 5 or 10 minutes.

Referring now to FIG. 21, hollow candy 402 comprises a transparent candy shell 420 formed of a palatable, ingestible material, for example sugar, sweet gelatin or other suitable candy material having a pleasant taste which will gradually dissolve or melt in the mouth.

Candy shell 420 may be supplemented externally, internally, or both internally and externally, with one or more transparent functional layers such as outer layer 422 to provide additional useful functionality, as will be exemplified below.

In the embodiment illustrated, candy shell 420 carries or is configured to provide a female connector 424 which is mateable with male connector 418. In the embodiment shown, light head 408 is configured and dimensioned to pass through female connector 424.

To mate with female connector 424 male connector 418 is provided with complementary threads, a bayonet fitting or other suitable fitting. Male connector 418 and female connector 424 may be a simple push fit, if desired, with or without a latching detent, optionally with tapering. Other structures for providing removable connectability between the two connectors will be apparent to those skilled in the art. The mating of male connector 418 and female connector 424 enables hollow candy 402 to be removably mounted on illuminator bar 400 in a structurally secure manner.

As illustrated, candy shell 420 comprises a hollow shell defining an interior volume to accommodate light head 408. Optionally candy shell may be generally ball-like or spherical. Candy shell 420 has a threaded radial bore constituting female connector 424 through which bore light head 408 may be received into the interior volume 425 of candy shell 420. It will be appreciated that there are many modifications and variations of this structure that may be made while implementing the objectives of the invention. Some of these are described below and others will be, or will become, apparent to those skilled in the art.

The simple structure illustrated, of the inventive candied photoapplicator, embodies a flexible design enabling the concepts of the invention to be implemented in a variety of different ways. For example, outer layer 422 can have antibacterial or antimicrobial properties, being provided with a suitable antibacterial or antimicrobial agent or agents that is slowly released as the layer dissolves in the mouth. A suitable antibacterial or antimicrobial substance or substances may also, or alternatively, be incorporated in candy shell 420.

In one useful embodiment of the invention hollow candy 402 is disposable and illuminator bar 400 is reusable.

As illustrated in FIG. 23, to use candied photoapplicator 404, a subject may grip illuminator bar 400 in one hand and insert the distal end of illuminator bar 400, bearing hollow candy 402, into the mouth. Also shown in FIG. 23, in a schematic manner, is a power supply 426 coupled to conductors 412 at the proximal end of illuminator bar 400. Power supply 426 can be any suitable supply including, but not limited to a rechargeable or disposable battery unit attachable to or integrated with illuminator bar 400, or contained within illuminator bar 400. Alternatively, power supply 426 may be a separate unit, optionally connectible with a local utility power supply, and may optionally also be connectible with illuminator bar 400 via a power cord.

The subject can manipulate candied photoapplicator 404 so that candy 402 is conveniently positioned in the mouth to be sucked, much like a lollipop. As it is sucked, candy 402 slowly dissolves in the mouth, releasing a liquid stream rich in any active agent or agents that have been provided in the candy. This action delivers the active agent or agents, at a controlled rate largely determined by the characteristics of candy 402, to topical sites in the oral cavity and in the pharyngeal region. Ultimately the saliva flow containing the active agent or agents may reach the stomach and gastrointestinal tract.

In the oral cavity, candied photoapplicator 404, as shown in FIG. 24, can usefully be juxtaposed between the tongue 430 and the pharynx 432, just short of a position that will induce a gagging reflex. Candied photoapplicator 404 can be supported by the subject's hand or hands, lips, teeth and tongue in any suitable manner that the subject finds convenient or desirable, depending upon the weight and bulk of photoapplicator 404. For example, illuminator bar body 406 may be held by one hand, candy 402 may rest on the tongue and be held approximately in place by modest pressure from the lips and/or the teeth. Other ways of using and manipulating candied photoapplicator 404 will be apparent to the treatment subject, may be indicated by a medical practitioner or will be, or become, apparent to those skilled in the art.

While candy 402 is being sucked and dissolved, light source 410 is activated, by operation of subject-activated switch operation or other suitable means. For example light switch 407 could be a motion sensor switch or could be responsive to moistening of candy head 402. Alternatively, in place of light switch 407, light source 410 may be always on when power is connected to conductors 412. As illustrated schematically in FIG. 24, light rays 431, emitted from light source 410 radiate outwardly in many directions, and especially distally of photoapplicator 404. Some light rays 434 impinge on the pharynx 432 and the tongue 430 whence they may be scattered in new directions 436. In this way, the oral cavity may be filled with light. Some of the scattered light may reach the back of the tongue and perhaps the tonsils as well.

In one embodiment of the invention, suitable active agents are incorporated in the one or more layers of candy shell 420 to deliver anti-bacterial and anti-inflammatory substances to the oral cavity as candy shell 420 dissolves in the mouth. Coupled with the anti-bacterial action of the light radiated into and scattered throughout the oral cavity, a multi-pronged treatment to improve halitosis and other conditions is provided. If desired a mild dosage of a local anesthetic, e.g. 4 percent XYLOCAINE (trademark), Astrazeneca LP, can be included in candy 402 to be delivered to the back of the tongue, as the candy dissolves, to suppress the gagging reflex.

Other embodiments of the invention may rely upon light alone for anti-microbial activity, with candy 402 being free of medically or pharmacologically active agents and consisting essentially or entirely of conventional candy ingredients to provide a pleasing taste sensation and a suitable rate of dissolution. Still further embodiments may employ additional or alternative active agents, for example anti-gagging agents or photosensitizers. With particular, but not exclusive application to children who may be entertained by the resulting coloration of their mouths, an outer or other layer of candy 402 may contain a foodstuffs-approved photosensitizing dye, desirably of a somewhat complementary color to light output from light source 410, as described herein, e.g. a red or blue food or pharmaceutical dye for a blue or red light source respectively. One such embodiment employs a blue or blue-green dye with an orange or red light source. It will be understood that one or more active ingredients complementary or synergistically acting, compatible active ingredients can be provided in candy shell 420 in a variety of ways.

As may be understood from the foregoing description, candy shell 420 comprises a flexible, time-sensitive, controlled release active agent delivery system. As described herein, one or more active agents may be selected from the group consisting of pharmaceutically or pharmacologically active agents, drugs or photosensitizers. Candy shell 420 may comprise a single layer containing a single active agent or multiple layers, one of which, for example an outer layer, contains a single active agent. Multiple active agents may be deployed in combination in a single layer of candy shell 420 or may be distributed through multiple layers, one agent per layer. It will be appreciated that an agent in an outer layer of candy shell 420 will tend to be released before an agent or agents in inner layers is or are released, although there may be some overlap as the layers dissolve unevenly. This mechanism permits a formulator to approximately time the release of one agent relatively to another. For example, a photosensitizer and optionally a gag-repressant, may be initially released, followed by an antimicrobial and finally an anti-inflammatory. The duration of release of each agent can be approximately controlled by selection of the design parameters of the respective candy shell layer, e.g. 414 or 422, as is further described elsewhere herein.

A wide range of various practical embodiments embodying concepts of the invention disclosed herein will be apparent to those skilled in the art. For example bar body 406 can be a relatively sturdy elongated block-like object that cannot practicably be swallowed and which might, for example have a length of from about 60 to about 300 mm, or desirably, from about 100 to about 200 mm and a girth at most locations along its length of from about 10 mm to about 80 mm, or desirably from about 20 mm to about 50 mm. With advantage, bar body can be flattened on two opposing surfaces in a region of its length appropriate for gripping between the teeth to help orient candied photoapplicator 404 in the oral cavity. If desired, illuminator bar 406 could be stick-like, with a rather small girth, perhaps about 6 to about 15 mm and optionally, candy shell 420 has a relatively enlarged three-dimensional shape so that such an embodiment of candied photoapplicator 404 has a lollipop-like appearance.

Alternatively, bar body 406 could have a plate-like or skeletal configuration, being intended to be gripped between the teeth at a number of locations, e.g one front and two side locations, to stably support light head 408 in a desired position, e.g slightly raised above the tongue in the posterior oral cavity.

Candy shell 420 can have any desired shape including fanciful decorative shapes such as fruits or animals shapes which can accommodate light head 408. Some useful embodiments of candy shell 420 in addition to spherical, or part-spherical can have modified shapes that are, for example flattened on one or more sides, approximately cube-shaped, cone-shaped or trumpet-shaped. The shape can be such as to be conveniently oriented in the mouth and to provide a pleasing presence in the mouth. If desired, one or more proximal surfaces of candy shell 420, e.g. in embodiments having a distally divergent shape such as frusto-conical or trumpet-like, can have an ingestible reflective coating to reflect radiation output from light 408 in the distal direction toward target treatment surfaces such as the back of the tongue or the tonsils. The coating may be an edible opaque material having a white, silver or light color. Alternatively, a suitably disposed reflective surface can be provided by employing adjacent shell layers of different materials having different refractive indices to provide a reflection boundary of a desired shape and location, e.g. proximally around light head 408, to reflect light and/or invisible electromagnetic energy, forwardly.

Candy shell 420 can have any desired largest transverse dimension, for example, from about 10 mm to about 50 mm, or from about 20 mm to about 30 mm. Optionally, candy shell 420 can have a minimum transverse dimension of from about 5 mm to about 30 mm. The dimensions suggested herein are for an average adult. Dimensions for a child or person of unusual anatomy can be varied accordingly.

In many useful embodiments, candy shell 420 comprises or consists largely, essentially or entirely of a relatively rigid or hard candy material that is slow dissolving. The candy material can be selected to provide a desired rate of dissolution and oral cavity life of candy shell 420 and/or a desired controlled release rate of incorporated actives.

In alternative embodiments, hollow candy 402 can be somewhat deformable, or formed in two or more hinged sections to be a snap fit over light head 408 which may accordingly be larger than the opening in female connector 424.

While one embodiment of candy shell 402, as illustrated is a self-supporting shell surrounding light head 408, other embodiments may comprise one or more masses or pieces of candy supported on a transparent plastic shell extending around or in front of light head 408. Optionally, the plastic shell may have smooth protrusions to anchor the candy.

It will be appreciated that replacement candy shells in a range or assortment of flavors, with or without out suitable medicaments or other appropriate adjuvants helpful to the treatments described herein may. Thus, a suitable marketing model for a consumer product may comprise modestly priced sale of the candied photoapplicator with profitably priced marketing of supplies for same, namely candy shells which consumers may purchase on a weekly, monthly or other basis.

While the invention has been described in the context of a handpiece intended for manipulation by a human user, the invention also includes robotic or remote operation of any of the devices described herein or modifications thereof designed for remote or robotic operation with either manual simulations or electronic actuation of the operator movements that would otherwise be required to conduct the procedure.

Many embodiments of the invention are suitable for, and the invention includes, the practice or use in a doctor's or dentist's office, or clinic, of photothermal and other treatments with photic or thermal energy of halitosis, and other oral or other bodily cavity infections with bacteria or other microorganisms on an out-patient or other basis. Self-administration and home use applications by a parent, nurse, caregiver or the like of embodiments of the invention will also be apparent to those skilled in the art and are embraced by the invention.

Consumer Product. The products and processes of the invention are suitable for use by consumers either for self-application or for one person to apply to another. If desired, particularly, although not exclusively, for consumer use, photothermal treatment instrument 10 can have a limited energy output intended to prevent user injury or abuse which may limit the maximum pulse intensity and/or the number of pulses that can be emitted in a given time period. For example the instrument may have a delay which prevents further operation for a period of from about 10 to about 30 minutes after a given number of pulses has been generated, for example from about 5 to about 10 pulses. Such a feature may prevent consumers or others overdosing and causing tissue damage.

Possible mechanism of action. While the invention is not limited by any particular theory, it will be understood by those skilled in the art that heat acts destructively on microorganisms by raising the temperature of their immediate environment. In contrast, a probable mechanism for the bactericidal properties of light is that of catalytic liberation of highly reactive species such as superoxides and free radicals which destroy sensitive molecules for example DNA in the bacteria.

More particularly, pursuant to the invention, but again without limiting the invention, it is hypothesized that in the tonsils and comparable anatomy, entrapment of proteinaceous detritus within the pores of the tonsil can create a closed anaerobic environment where anaerobic bacteria can build up, damaging the tissue structure and initiating an inflammatory response. As part of their reproduction and metabolism process, the bacteria produce photochemically active porphyrins, and the like, which yield singlet oxygen upon exposure to light, especially at blue wavelengths. The singlet oxygen can react with bacterial membrane species to destroy the bacteria.

Summarizing, the invention provides, in one aspect, apparatus for treating halitosis comprising a sprayer for spraying a photodynamically bactericidal compound on to a target tissue surface harboring bacteria causing halitosis and a rinsing device to rinse surplus compound from the target tissue to prevent the photodynamically active bactericidal compound from diffusing into deeper layers of tissue to control harmful side effects. The apparatus can comprise at least two pipes, one for pipe for spraying compound and another pipe for rinsing and may optionally include a pipe for delivering oxygen to the target site.

In addition, the apparatus can comprise a guide to prevent touching of the back of the tongue and creating a gagging reflex. In one embodiment the apparatus can be operated hands free. To this end, the apparatus can comprise a spacer to be held between the patient's teeth and prop the mouth open, and a mount pivotally supporting the treatment applicator for tilting movement within the mouth.

The treatment applicator can be slidable in a groove enabling the applicator to move forward or backward until a desired treatment position is achieved, and a tightening device or devices can be provided to enable a selected position to be secured for the treatment duration.

The invention also provides, in other aspects, apparatus for the optical treatment of the back of the tongue for a duration longer than 5 minutes as well as apparatus for the optical treatment of the back of the tongue which is capable of hands-free operation and is capable of being secured in position in the patient's oral cavity by attachment to the patient's anatomy.

In a still further aspect, the invention provides a candied photoapplicator for delivering light to treat microorganisms populating a target site in the oral-pharyngeal cavity, the candied photoapplicator comprising:
a) an illuminator member;
b) a light source supported on the illuminator member to illuminate the target site in the oral cavity; and
c) a candy component supported by the illuminator member, the candy component being suitable for sucking by the subject while the illuminator member illuminates the oral cavity.

The candy component can be hollow and can accommodate the light source. Optionally the candy component can comprise candy material incorporating therapeutic agents or adjuncts for delivery to the treatment site. The candy component can be replaceably attachable to the illuminator member.

The candied photoapplicator can be designed to be resistant to ingestion of the whole device or any of its parts, to resist biting by the subject, and to resist fragmentation into pieces. Optionally, the illuminator bar can be made to be too large to be swallowed by the intended subject and the hollow candy can be sized and shaped to be comfortably accommodated in the subject's mouth. The illuminator bar can project externally of the oral cavity during use to illuminate the oral-pharyngeal and can be readily gripped and manipulated.

In one embodiment, of the candied photoapplicator embodiment of the invention, the illuminator bar comprises:
i) a bar body;
ii) a light head mounted on and supported at the distal end of the bar body; and
iii) optionally, a light switch mounted on the bar body. The light source can comprise one or more light-emitting diodes, for example, multiple light-emitting diodes having different operating wavelengths.

Staining of bacteria to enhance the photolytic action while useful in many embodiments, is not essential, but can be employed if desired. It is a feature of some embodiments of the invention that they may be effectively practiced to control unstained microorganisms. Employment of combined heat and light energy, pursuant to the invention, provides the unexpected benefit that elevating the target temperature may accelerate the photolytic reactions enhancing the bactericidal efficacy of the treatment.

If desired, the halitosis treatment methods and apparatus of the invention may be augmented by treating the target surfaces with one or more chemical or pharmaceutical anti-infective agents which may be administered in any suitable manner, for example by spray, drops or vapors, as an aerosol, or optionally with the assistance of a nebulizer. Suitable agents, dosages and administration methods and devices are known to the art. For example, some are described in Osbakken et al. U.S. Pat. No. 6,576,224, the disclosure of which is hereby incorporated herein by this specific reference thereto. Those skilled in the art will be able to select suitable or especially useful such an anti-infective and an administration method and device in light of the disclosure herein. Such adjunctive treatment may be effected at any appropriate time in relation to the light-utilizing therapy, for example immediately prior thereto, from 1 to 6 hours prior thereto and/or on an ongoing basis, daily, twice daily or more frequently, between light-based treatments.

Though described in relation to the treatment of nondental target sites in the upper respiratory tract, it will be understood that the principles of the invention can be applied to the treatment of target sites, and especially mucous tissues, in other externally accessible bodily cavities including the nasal and sinus cavities in the sin-nasal tract.

Treatment of nonhuman mammals. While the invention has been described in relation to the control of microorganisms in nondental cavities of the upper respiratory tract in humans, it will be understood that the principles of the invention can also be applied to non-human mammals including for example, horses, cattle, sheep and other husbanded animals, pets such as dogs and cats, laboratory animals for example mice, rats and primates, animals employed for sports, entertainment, law enforcement, draft usage, zoological or other purposes.

Dental Sites of Treatment. In addition to treatment of the described nondental cavity sites, the invention can be applied to the treatment of other bodily sites, if desired, including for example, dental and periodontal sites. One embodiment of the invention includes the treatment of deep periodontal pockets identified as being locations of halitosis-causing bacteria by the methods, instruments, devices or apparatus of the invention as described hereinabove.

Disclosures Incorporated. The entire disclosure of each and every United States patent and patent application, each foreign and international patent publication, of each other publication and of each unpublished patent application that is referenced in this specification or elsewhere in this patent application, is hereby incorporated herein, in its entirety, by the respective specific reference that has been made thereto.

While illustrative embodiments of the invention have been described above, it is, of course, understood that many and various modifications will be apparent to those of ordinary skill in the relevant art, or may become apparent as the art develops. Such modifications are contemplated as being within the spirit and scope of the invention or inventions disclosed in this specification.

The invention claimed is:

1. A method for the treatment of halitosis comprising:
determining whether a subject is presenting with a symptom of halitosis by detecting whether oral odor is emanating from the subject;
applying visible light energy to a nondental target site selected from the group consisting of the back of the tongue, a tonsil, multiple tonsils, the throat and the pharynx of a subject presenting with a symptom of halitosis, the target site being determined to harbor a colony of anaerobic microorganisms generating malodorous gas wherein the visible light energy is applied to the target site at a wavelength and an intensity and for a duration effective to control the colony of microorganisms; and
applying to the target site longer wavelength energy comprising heat, RF or microwave energy or combinations of two or more of said energies.

2. A method according to claim 1 wherein the heat energy is provided by an infrared radiative source, a convective source, a conductive source or by in situ induction by RF or microwave energy.

3. A method according to claim 1 wherein the RF energy is in a range of from about 300 kHz to about 100 MHz.

4. A method according to claim 1 wherein the microwave energy has a frequency or frequencies in the range of from about 100 MHz to about 50,000 MHz.

5. A method according to claim 3 wherein the RF energy has an output power of from about 5 to about 200 W, a pulse duration of from about 1 to about 500 msec and a pulse rate of from about 0.1 to about 10 pulses per second.

* * * * *